(12) United States Patent
Mizuno et al.

(10) Patent No.: US 10,137,064 B2
(45) Date of Patent: Nov. 27, 2018

(54) FOAMING CLEANSER

(71) Applicant: L'OREAL, Paris (FR)

(72) Inventors: Hiroyasu Mizuno, Kawasaki (JP);
Anne-Laure Bernard, Clark, NJ (US)

(73) Assignee: L'OREAL, Paris (FR)

( * ) Notice: Subject to any disclaimer, the term of this patent is extended or adjusted under 35 U.S.C. 154(b) by 37 days.

(21) Appl. No.: 15/315,070

(22) PCT Filed: May 29, 2015

(86) PCT No.: PCT/IB2015/054059
§ 371 (c)(1),
(2) Date: Nov. 30, 2016

(87) PCT Pub. No.: WO2015/181789
PCT Pub. Date: Dec. 3, 2015

(65) Prior Publication Data
US 2017/0196780 A1    Jul. 13, 2017

(30) Foreign Application Priority Data

May 30, 2014    (JP) .................................. 2014-113211

(51) Int. Cl.
| | | |
|---|---|---|
| C11D 3/37 | (2006.01) | |
| A61K 8/04 | (2006.01) | |
| A61K 8/44 | (2006.01) | |
| A61K 8/45 | (2006.01) | |
| A61K 8/81 | (2006.01) | |
| A61Q 19/10 | (2006.01) | |
| A61K 8/41 | (2006.01) | |
| A61K 8/34 | (2006.01) | |
| A61K 8/36 | (2006.01) | |
| A61K 8/42 | (2006.01) | |
| A61K 8/86 | (2006.01) | |
| A61Q 1/14 | (2006.01) | |
| A61Q 19/00 | (2006.01) | |

(52) U.S. Cl.
CPC ............... *A61K 8/046* (2013.01); *A61K 8/04* (2013.01); *A61K 8/345* (2013.01); *A61K 8/361* (2013.01); *A61K 8/41* (2013.01); *A61K 8/42* (2013.01); *A61K 8/44* (2013.01); *A61K 8/45* (2013.01); *A61K 8/817* (2013.01); *A61K 8/8147* (2013.01); *A61K 8/8152* (2013.01); *A61K 8/86* (2013.01); *A61Q 1/14* (2013.01); *A61Q 19/007* (2013.01); *A61Q 19/10* (2013.01); *A61K 2800/413* (2013.01); *A61K 2800/596* (2013.01)

(58) Field of Classification Search
CPC ........ A61Q 5/02; A61Q 19/10; A61K 8/8152; C11D 3/3765
USPC ...................... 424/70.16; 510/475
See application file for complete search history.

(56) References Cited

U.S. PATENT DOCUMENTS

| | | | |
|---|---|---|---|
| 2008/0280797 A1* | 11/2008 | Compain | ............... A61K 8/042 510/136 |
| 2011/0152150 A1* | 6/2011 | Bernard | ................. A61K 8/046 510/136 |
| 2011/0275552 A1 | 11/2011 | Patel et al. | |
| 2012/0046210 A1 | 2/2012 | Patel et al. | |

FOREIGN PATENT DOCUMENTS

| | | |
|---|---|---|
| JP | 2000-038593 A | 2/2000 |
| JP | 2013-155151 A | 8/2013 |
| WO | 2013/186720 A2 | 12/2013 |
| WO | 2015/071298 A2 | 5/2015 |

OTHER PUBLICATIONS

"Nourish the Skin by Washing—Development of Emollient-Rich Shower Products." In-Cosmetics Hamburg, pp. 1-28, XP055211393, 2014.
"Continuous Spray Shampoo." Mintel GNPD, XP002724386, 2011.
"Mild Surfactants for Personal Care Applications." pp. 1-39, XP055211614, 2016.
Jones. "Multifunctional Synthetic Rheology Modifiers for Personal Care Formulations: More Than Just Thickeners." Rohm and Haas Personal Care, pp. 1-23, XP007909943, 2005.
Sep. 21, 2015 Search Report issued in International Patent Application No. PCT/IB2015/054059.
"Queen of the Night Shower & Oil Pearls.", Mintel GNPD, XP002744169, Jun. 1, 2013.

(Continued)

*Primary Examiner* — Gregory E Webb
(74) *Attorney, Agent, or Firm* — Oliff PLC

(57) ABSTRACT

The invention relates to a foaming cleanser cosmetic composition containing, in a physiologically acceptable medium: —a surfactant system comprising (i) at least one N—(C6-C30)acyl-amino based surfactant and (ii) at least one amphoteric surfactant chosen from betaines or (C8-C20) alkyl betaines, (C8-C20)alkylamido(C1-C6)alkylbetaines and mixtures thereof; and—at least one non associative crosslinked copolymer or acrylic acid and/or methacrylic acid, and optionally of (C1-C4)alkyl esters thereof, wherein said N—(C6-C30)acyl-amino based surfactant being present in the surfactant system in a major weight amount, and the surfactant system being present in the composition in an amount of less than 15% by weight relative to the total weight of the composition. The invention also relates to a process for cleansing keratin materials, which consists in applying the said composition to the said keratin materials, in working it into a foam and then in rinsing off the said composition, as well as the cosmetic use of the composition as defined above, for removing makeup and/or cleansing the skin, the hair and/or mucous membranes, or for skincare.

24 Claims, No Drawings

(56) References Cited

OTHER PUBLICATIONS

"Piña Colada Exfoliating Shower Gel." Mintel GNPD, XP002744170, Aug. 1, 2012.
Mar. 19, 2018 Office Action issued in Japanese Application No. 2014-113211.

* cited by examiner

FOAMING CLEANSER

The present invention relates to a composition, in particular a foaming cleanser composition, in particular a cosmetic composition, containing a surfactant system comprising (i) at least one N—(C6-C30)acyl-amino based surfactant and (ii) at least one amphoteric surfactant chosen from betaines or (C8-C20)alkyl betaines, (C8-C20)alkylamido(C1-C6)alkylbetaines, and mixtures thereof; and at least one non associative crosslinked copolymer of (meth) acrylic acid, and of (C1-C4)alkyl esters thereof, said N—(C6-C30)acyl-amino based surfactant being present in the surfactant system in a major weight amount and the surfactant system being present in the composition in an amount of less than 15% by weight relative to the total weight of the composition, for providing foam of improved quality and density and achieving skin mildness.

We know from document US2012/0046210 a clear liquid composition comprising alkanoyl glycinate, amphoteric, alkyl sulphate and specific acrylate polymers. However, the nature of the used acrylate polymer is different as exhibiting associative properties, it follows that the foam quality is not satisfying when high amount of thickener is present in the composition.

Document US2005/0054547 moreover describes a mild cleansing composition comprising a) an anionic surfactant, b) a hydrophobically modified, crosslinked, anionic acrylic copolymer wherein the weight ratio of component a) to component b) is fixed, and wherein the composition is mild to the skin and/or eyes and is substantially free of non-ionic surfactants. However, the disclosed compositions are devoid of N-acyl-amino based surfactant, resulting in less foaming performance that do not meet with consumer needs especially for Asian consumers.

None of the disclosed composition achieves completely satisfying quality and density foaming properties while giving mildness to the skin simultaneously.

Consequently, there is a need for foaming cleansing compositions that are free of the abovementioned drawbacks and allowing combining foam quality and respect of the skin.

The inventors have demonstrated that the combination of a specific surfactant system with at least one non associative crosslinked copolymer of acrylic acid and/or methacrylic acid, and optionally of esters thereof, makes it possible to achieve satisfactory foam quality while achieving skin mildness.

One subject of the present invention is thus a foaming cleanser cosmetic composition containing, in a physiologically acceptable medium:
  a surfactant system comprising (i) at least one N—(C6-C30)acyl-amino based surfactant, and (ii) at least one amphoteric surfactant chosen from betaines or (C8-C20)alkyl betaines, (C8-C20)alkylamido(C1-C6)alkylbetaines, and mixtures thereof; and
  at least one non associative crosslinked copolymer of acrylic acid and/or methacrylic acid, and optionally of esters thereof,
wherein said N—(C6-C30)acyl-amino based surfactant is present in the surfactant system in a major weight amount and the surfactant system being present in the composition in an amount of less than 15% by weight relative to the total weight of the composition.

For the purposes of the present invention the term "major amount" means that the N—(C6-C30)acyl-amino based surfactant is present in the surfactant system in a greater amount than each of the other surfactants taken alone, present within said surfactant system, with respect to the total weight of the surfactant system.

In particular, the N—(C6-C30)acyl-amino based surfactant may be present it in an amount over 40% by weight, in particular over 42%, more particularly over 45%, or 50% by weight with respect to the total weight of the surfactant system.

According to another of its aspects, a subject of the invention is also a process for cleansing keratin materials, which consists in applying to the said keratin materials a composition according to the invention, in working the said composition into a foam and then in rinsing off the said composition, especially with water.

A subject of the present invention is also the cosmetic use of the composition as defined above, for removing makeup and/or cleansing the skin, the hair and/or mucous membranes, or for skincare.

The compositions of the invention may be used in the field of the makeup removal and cleansing of facial or bodily skin, the hair, including the scalp, and mucous membranes such as the lips.

According to some particular embodiments of the present invention and as it will be apparent from the following description, further skin care benefits may be obtained by deposition of additional ingredients on the skin, such as moisturizing after washing the skin or such as anti-shine effect.

For the purposes of the present invention, the term "physiologically acceptable medium" means a medium that is suitable for the topical administration of a composition.

A physiologically acceptable medium is preferably a cosmetically or dermatologically acceptable medium, that is to say a medium which is devoid of unpleasant odour or appearance and which is entirely compatible with the topical administration route.

Such a medium is in particular considered as physiologically acceptable when it does not cause the user any unacceptable stinging, tautness or redness.

Non Associative Crosslinked Copolymers of Acrylic Acid and/or Methacrylic Acid

The composition according to the invention comprises at least one non associative crosslinked copolymer of (meth) acrylic acid, and of (C1-C4) alkyl esters thereof.

For the purpose of the present invention, the term "non associative polymer" means that the polymer does not have the behaviour an associative polymer, i.e. a hydrophilic polymer, more particularly comprising at least one hydrophilic regions and at least one hydrophobic region; that is capable, in an aqueous medium, of reversibly associating with each other or with other molecules.

According to a particular embodiment, said non associative crosslinked copolymers of (meth)acrylic acid are able to form a microgel.

According to the present invention, a microgel is a gel wherein at least 90%, preferably 95%, more preferably all of the gel is in the form of particles.

According to one embodiment, the at least one crosslinked copolymer disclosed herein may be in the form of a dispersion in water. The number-average size of the copolymer particles in the dispersion generally ranges from 10 to 500 nm, for example, from 20 to 200 nm and further, for example, from 50 to 150 nm.

The non-associative crosslinked copolymers of (meth) acrylic acid, and of (C1-C4)alkyl esters thereof, acts as a thickening polymer and also contributes to the ability of the composition to deposit additional ingredients when present, as for example fillers or a triglyceride oil, even after rinsing-off thereof.

The copolymers disclosed herein are partially or totally crosslinked with at least one standard crosslinking agent. The at least one crosslinking agent can be chosen, for example, from polyunsaturated compounds, such as polyethylenically unsaturated compounds. For example, these compounds can be chosen from polyalkenyl ethers of sucrose, polyalkenyl ethers of polyols, diallyl phthalates, divinylbenzene, allyl (meth)acrylate, ethylene glycol di(meth)acrylate, methylenebisacrylamide trimethylolpropane tri(meth)acrylate, diallyl itaconate, diallyl fumarate, diallyl maleate, zinc (meth)acrylate, castor oil derivatives and polyol derivatives manufactured from unsaturated carboxylic acids.

For the purpose of the present invention, the non associative crosslinked copolymers of (meth)acrylic acid means that the copolymer comprises at least one acrylic acid unit or one methacylic acid unit or a mixture thereof. The copolymer comprises further units such as units formed by an ester of acrylic acid or methacrylic acid, preferably of acrylic acid, comprising less than 6 carbon atoms: i.e. a $C_1$-$C_4$ alkylacrylate for example, chosen from methyl acrylate, ethyl acrylate and butyl acrylate, called hereinafter "simple ester".

According to a particular embodiment, a non associative crosslinked copolymer according to the present invention comprises at least an acrylic acid unit. According to a further embodiment, a non associative crosslinked copolymer according to the present invention comprises at least a methacrylic acid unit. According to another embodiment, a non associative crosslinked copolymer according to the present invention comprises at least an acrylic acid unit and a methacrylic acid unit.

In a particular embodiment, the non associative crosslinked copolymer may comprise another monomer that is different from (meth)acrylic acid and from (C1-C4)alkyl ester thereof. For example, such monomer may be selected from esters of (C4-C30)carboxylic acid, preferably (C6-C12) carboxylic acid, and vinylic alcohol.

We can mention the crosslinked copolymer of vinyl neodecanoate and one or more monomers of acrylic acid, methacrylic acid or one of their $C_1$-$C_4$ esters crosslinked with an allyl ether of trimethylolpropane or pentaerythritol such as the product sold under the commercial name ACULYN 38® (INCI name: ACRYLATES/VINYL NEODECANOATE CROSSPOLYMER) sold by THE DOW CHEMICAL COMPANY.

As other examples of such non-associative crosslinked copolymers of acrylic acid and/or methacrylic acid, can be mentioned the non-associative crosslinked copolymers of acrylic acid and/or methacrylic acid and $C_1$-$C_4$ alkyl esters thereof.

As an example of such non-associative crosslinked copolymers of acrylic acid and/or methacrylic acid and ($C_1$-$C_4$) alkyl esters thereof, can be mentioned:

i) The crosslinked copolymers of acrylic acid and/or methacrylic acid and of an ester thereof comprising less than 6 carbon atoms, preferably a $C_1$-$C_4$ alkyl ester, and such as the copolymer sold under the commercial name ACULYN 33® by the company THE DOW CHEMICAL COMPANY and having the INCI name: ACRYLATES COPOLYMER.

ii) The crosslinked copolymers comprising at least one methacrylic acid unit and at least one $C_1$-$C_4$ alkyl acrylate unit. These copolymers are described, for example, in Patent Application no WO 01/76552.

As used herein, the crosslinked copolymer comprising at least one methacrylic acid unit and at least one $C_1$-$C_4$ alkyl acrylate unit means a crosslinked copolymer comprising at least one methacrylic acid unit and at least one alkyl acrylate unit, wherein the alkyl acrylate unit is chosen from $C_1$-$C_4$ alkyl acrylates.

In the crosslinked copolymers disclosed herein, the methacrylic acid unit can be present, for example, in an amount ranging from 20% to 80% by weight, such as from 25% to 70% by weight, and further such as from 35% to 60% by weight, relative to the total weight of the copolymer.

In the crosslinked copolymer disclosed herein, the (C1-C4)alkyl acrylate unit can be present, for example, in an amount ranging from 15% to 80% by weight, such as from 25% to 75% by weight and further such as from 40% to 65% by weight, relative to the total weight of the copolymer. The (C1-C4)alkyl acrylate unit can be chosen, for example, from methyl acrylate, ethyl acrylate and butyl acrylate. In one embodiment, the (C1-C4)alkyl acrylate unit is ethyl acrylate.

Use can be made, for example, of the crosslinked copolymers comprising at least one methacrylic acid unit and at least one ethyl acrylate unit like the one sold under the name CARBOPOL AQUA SF-1® by the company NOVEON (INCI name: acrylates copolymer).

Thus, in a preferred embodiment, the non-associative crosslinked copolymers of acrylic acid and/or methacrylic acid, and (C1-C4) alkyl esters thereof, is selected from:
  a crosslinked copolymer of acrylic acid and/or methacrylic acid and of an ester thereof comprising less than 6 carbon atoms, preferably a $C_1$-$C_4$ alkyl ester thereof,
  a crosslinked copolymer comprising at least one methacrylic unit and at least one $C_1$-$C_4$ alkyl acrylate unit, for example a ethyl acrylate unit,
  a crosslinked copolymer of vinyl neodecanoate and one or more monomers of acrylic acid, methacrylic acid or one of their (C1-C4) alkyl esters crosslinked with an allyl ether of trimethylolpropane or pentaerythritol, and mixtures thereof.

The at least one non-associative crosslinked copolymers of acrylic acid and/or methacrylic acid, and of $C_1$-$C_4$ alkyl esters thereof, is included in the composition according to the present invention in an active material content greater than or equal to 1% by weight, in particular greater than or equal to 1.5% by weight, more particularly greater than or equal to 2% by weight relative to the total weight of the composition, for example in a content ranging from 1% to 10% by weight, from 1.5% to 10% by weight, from 2% to 8% by weight, or from 2% to 4% by weight relative to the total weight of the composition.

Surfactant System

The composition according to the invention contains a surfactant system that gives the composition its foaming nature. The said surfactant system comprises (i) at least one N—(C6-C30)acyl-amino based surfactant, and (ii) at least one amphoteric surfactant chosen from betaines or (C8-C20) alkyl betaines, (C8-C20)alkylamido(C1-C6)alkylbetaines, and mixtures thereof.

The surfactant system is present in the composition in an amount of less than 15% by weight relative to the total weight of the composition.

According to one particular embodiment, the surfactant system is present in the composition is a content less or equal to than 12% by weight, in particular less than or equal to 10.5% by weight, and more particularly less than or equal to 8.5% by weight, relative to the total weight of the composition.

According to a more particular embodiment, the surfactant system is present in the composition in an amount ranging from 0.1 to 12% by weight, in particular from 2 to 10% by weight, more particularly from 4 to 8.5% by weight relative to the total weight of the composition.

Foaming surfactants are detergents and differ from emulsifiers in the value of their HLB (Hydrophilic-Lipophilic Balance), the HLB being the ratio of the hydrophilic part to the lipophilic part in the molecule. The term "HLB" is well known to a person skilled in the art and is described, for example, in "The HLB system. A time-saving guide to Emulsifier Selection" (published by ICI Americas Inc., 1984). For emulsifiers, the HLB generally ranges from 3 to 8 for the preparation of W/O emulsions and from 8 to 18 for the preparation of O/W emulsions, whereas foaming surfactants generally have an HLB of greater than 20.

N—(C6-C30)acyl-amino Based Surfactant

The N—(C6-C30)acyl amino based surfactant that may be present in the composition according to the invention may be chosen in particular among N—(C6-C30)acyl aminoacid based surfactant such as glycine derivatives (glycinates) like N—(C6-C30)acyl glycinate based surfactants.

The amino acid moiety of N—(C6-C30)acyl aminoacid based surfactant may be for example chosen from glycine, alanine, leucine, isoleucine, valine, arginine, glutamic acid, aspartic acid, and preferably glycine.

The N-acyl moiety of the N—(C6-C30)acyl amino based surfactant may comprise from 6 to 30 carbon atoms, preferably from 8 to 22 carbon atoms, even more preferably from 8 to 18 carbon atoms.

Preferably, the N—(C6-C30)acyl amino based surfactant is a salt of N(C6-C30)-acyl aminoacid, preferably an alkali metal salt, and even more preferably a potassium or sodium salt.

Examples of N—(C6-C30)acyl amino based surfactant according to the present invention include:
- (C6-C30)acyl glycinates, and preferably (C8-C22)acylglycinates, even more preferably (C8-C18)acylglycinates, such as alkali salts N-cocoyl glycinate, like the one sold under the name Amilite GCK 12H® by the company Ajinomoto,
- (C6-C30)acylalaninates, and preferably (C12-C28)acylalaninates, such as sodium N-lauroyl N-methyl amidopropionate sold under the name Sodium Nikkol Alaninate LN30® by the company Nikkol, or sold under the name Alanone ALE® by the company Kawaken, and triethanolamine N-lauroyl N-methyl alanine sold under the name Alanone Alta® by the company Kawaken,
- (C6-C30)acylglutamates, especially (C6-C24)- or even (C12-C20)acylglutamates, such as triethanolamine monococoyl glutamate sold under the name Acylglutamate CT-12® by the company Ajinomoto, or triethanolamine lauroyl glutamate sold under the name Acylglutamate LT-12® by the company Ajinomoto, or stearoylglutamates like disodium stearoylglutamate;
- (C6-C30)acylaspartates, especially of (C6-C24)acylaspartates, such as the mixture of triethanolamine N-lauroyl aspartate and of triethanolamine N-myristoyl aspartate, sold under the name Asparack® by the company Mitsubishi.

In a particular embodiment, the N—(C6-C30)acyl amino based surfactant is chosen from alkali salts of N-cocoyl glycinate, especially among potassium N-cocoyl glycinate, sodium N-cocoyl glycinate, or a mixture thereof, preferably potassium N-cocoyl glycinate.

Sodium N-cocoyl glycinate which may be contained in a product sold under the name Amilite GCS-12K® and potassium N-cocoyl glycinate which may be comprised in a product sold under the name Amilite GCK 12H® by the company Ajinomoto, may in particular be implemented in the foaming composition according to the present invention.

The N—(C6-C30)acyl amino based surfactant may be present in the composition according to the present invention in an amount ranging from 0.1 to 6% by weight, in particular from 1 to 5% by weight, and more particularly from 2 to 4% by weight, with respect to the total weight of composition.

Amphoteric Surfactant

The amphoteric surfactant is chosen from betaines or (C8-C20)alkyl betaines, (C8-C20)alkylamido(C1-C6)alkylbetaines, and mixtures thereof.

Mention may in particular be made, as betaines, of (C8-C20)alkyl betaines, such as, for example, coco betaine, such as the product sold under the name Dehyton AB-30® by the company Cognis, lauryl betaine, such as the product sold under the name Genagen KB® by the company Clariant, oxyethylenated (10 EO) lauryl betaine, such as the product sold under the name Lauryl Ether (10 EO) Betaine® by the company Shin Nihon Rica, or oxyethylenated (10 EO) stearyl betaine, such as the product sold under the name Stearyl Ether (10 EO) Betaine® by the company Shin Nihon Rica.

Mention may be made, among (C8-C20)alkylamido(C1-C6)alkylbetaines and derivatives thereof, for example, of cocamidopropyl betaine, sold under the name Lebon 2000 HG® by the company Sanyo or sold under the name Empigen BB® by the company Albright & Wilson, or lauramidopropyl betaine, sold under the name Rewoteric AMB12P® by the company Witco.

Preferably, the amphoteric surfactant is chosen from (C8-C20)alkyl betaines and (C8-C20)alkylamido(C1-C6)alkylbetaines, and mixture thereof and preferably among coco betaine, lauryl betaine, oxyethylenated (10 EO) lauryl betaine, oxyethylenated (10 EO) stearyl betaine, cocamidopropyl betaine and mixtures thereof, and more preferably is selected from lauryl betaine, coco betaine and mixtures thereof and still more preferably is lauryl betaine.

The amphoteric surfactant may be present in the composition according to the present invention in an amount ranging from 0.1 to 6% by weight, in particular from 0.5 to 5% by weight, and more particularly from 1 to 4% by weight, with respect to the total weight of the composition.

According to a particular embodiment, the weight ratio between the N—(C6-C30)acyl amino based surfactant (i) and the amphoteric surfactant (ii) ranges from 1:1 to 5:2 and preferably between 10:9 to 2:1.

Optional Salt of $C_8$-$C_{20}$ Fatty Acid

According to a particular embodiment, the surfactant system further may comprise a soap.

Generally the soap used is alkali metal soap and/or combination of metal and organic soap of fatty acid with carbon chain ranging from $C_8$ to $C_{20}$ more preferably from $C_{12}$ to $C_{18}$ and most preferably from $C_{12}$ to $C_{14}$.

The fatty acid can in particular be selected among the caproic acid, capric acid, caprylic acid, oleic acid, linoleic acid, lauric acid, the myristic acid, the stearic acid, the palmitic acid and mixtures thereof.

More particularly, the fatty acid which is suitable for the present invention is present in the form of a mixture of fatty acids and is contained in coconut oil, also known as coprah oil or copra oil.

The alkali metals that may be used for the soap include sodium, potassium, lithium and their mixtures. Preferably, the alkali metal is potassium.

In a preferred embodiment, the alkali metal soap is potassium cocoate, also known as potassium coco soap that originates from the fatty acids present in coconut oil as mentioned above. For example, potassium cocoate may be present in admixture with potassium N-cocoyl glycinate (N—(C6-C30)acyl amino based surfactant) like in a product sold under the name Amilite GCK-12H® by the company Ajinomoto as explained above and as shown in the examples of the present invention.

The metal soaps that may be used include zinc laurate, magnesium stearate, magnesium myristate, zinc stearate and their mixtures.

The metal of the metal soap can in particular be zinc or magnesium.

The neutralization rate of fatty acid may range from 70 to 90%, most preferably in the range from 80 to 85%.

Non-limiting examples of alkalis from metal/nonmetal/organic source which may be used for saponification of fatty acids are hydroxides, such as alkali metal hydroxides, for example sodium hydroxide or potassium hydroxide or such as alkaline-earth metal hydroxides, for example magnesium hydroxide, or even such as ammonium hydroxide, silicates of potassium, sodium, calcium, or organic bases such as ethanolamines, for example triethanolamine, N-methylglucosamine, amino propanol and their derivatives, lysine, arginine and their salts such as guanadine salts.

The salt of $C_8$-$C_{20}$ fatty acid may be present in the composition according to the present invention in an amount ranging from 0.1 to 6% by weight, in particular from 0.5 to 5% by weight, and more particularly from 1 to 4% by weight, with respect to the total weight of the composition.

According to a particular embodiment, the weight ratio between the salt of $C_8$-$C_{20}$ fatty acid and the N—(C6-C30) acyl amino based surfactant ranges from 1:10 and 8:10, in particular from 2:10 to 6:10.

According to a particular embodiment, the weight ratio between the N—(C6-C30)acyl amino based surfactant (i)+ salt of C8-20 fatty acid and the amphoteric surfactant (ii) ranges from 5:1 to 1:1 and preferably between 4:1 to 2:1.

Additional Surfactants

The foaming composition may comprise additional surfactants, which may be selected from anionic, amphoteric (or zwitterionic), nonionic and/or cationic foaming surfactants, and mixtures thereof, and that are different from the surfactants of the main surfactant system as described above.

The foaming composition may comprise additional surfactants, which may be selected from anionic, amphoteric (or zwitterionic), nonionic and/or cationic non foaming surfactants, and mixtures thereof, and that are different from the surfactants of the main surfactant system as described above.

Anionic Surfactants

The composition according to the invention may also comprise one or more anionic surfactants.

The term "anionic surfactant" means a surfactant comprising, as ionic or ionizable groups, only anionic groups.

In the present description, a species is termed as being "anionic" when it bears at least one permanent negative charge or when it can be ionized as a negatively charged species, under the conditions of use of the composition of the invention (for example the medium or the pH) and not comprising any cationic charge.

The anionic surfactants may be sulfate, sulfonate and/or carboxylic (or carboxylate) surfactants. Needless to say, a mixture of these surfactants may be used.

It is understood in the present description that:
carboxylate anionic surfactants comprise at least one carboxylic or carboxylate function (—COOH or —COO$^-$) and may optionally also comprise one or more sulfate and/or sulfonate functions;
the sulfonate anionic surfactants comprise at least one sulfonate function (—SO$_3$H or —SO$_3^-$) and may optionally also comprise one or more sulfate functions, but do not comprise any carboxylate functions; and
the sulfate anionic surfactants comprise at least one sulfate function but do not comprise any carboxylate or sulfonate functions.

The anionic surfactants that may be present in the composition according to the invention may be chosen in particular from anionic derivatives of proteins of plant origin or of silk proteins, phosphates and (C6-C30)alkyl phosphates, carboxylates, sulfosuccinates, (C6-C30) acyl or alkyl acids, sulfates, sulfonates, isethionates, taurates, (C6-C30)alkyl sulfoacetates, polypeptides, anionic derivatives of (C6-C30) alkyl polyglucoside, and soaps (fatty acid salts), and mixtures thereof.

a) Anionic derivatives of proteins of plant origin are protein hydrolysates containing a hydrophobic group, it being possible for the said hydrophobic group to be naturally present in the protein or to be added by reaction of the protein and/or of the protein hydrolysate with a hydrophobic compound. The proteins are of plant origin or are derived from silk, and the hydrophobic group may in particular be a fatty chain, for example an alkyl chain comprising from 10 to 22 carbon atoms. As anionic derivatives of proteins of plant origin, mention may more particularly be made of apple, wheat, soybean or oat protein hydrolysates comprising an alkyl chain having from 10 to 22 carbon atoms, and salts thereof. The alkyl chain may especially be a lauryl chain and the salt may be a sodium, potassium and/or ammonium salt.

Thus, as protein hydrolysates comprising a hydrophobic group, mention may be made, for example, of salts of protein hydrolysates where the protein is a silk protein modified by lauric acid, such as the product sold under the name Kawa Silk by Kawaken; salts of protein hydrolysates where the protein is a wheat protein modified by lauric acid, such as the potassium salt sold under the name Aminofoam W OR by the company Croda (CTFA name: potassium lauroyl wheat amino acids) and the sodium salt sold under the name Proteol LW 30 by the company SEPPIC (CTFA name: sodium lauroyl wheat amino acids); salts of protein hydrolysates where the protein is an oat protein comprising an alkyl chain having from 10 to 22 carbon atoms and more especially salts of protein hydrolysates where the protein is an oat protein modified by lauric acid, such as the sodium salt sold under the name Proteol OAT (30% aqueous solution) by the company SEPPIC (CTFA name: sodium lauroyl oat amino acids); or salts of apple protein hydrolysates comprising an alkyl chain having from 10 to 22 carbon atoms, such as the sodium salt sold under the name Proteol APL (30% aqueous glycol solution) by the company SEPPIC (CTFA name: sodium cocoyl apple amino acids). Mention may also be made of the mixture of lauroyl amino acids (aspartic acid, glutamic acid, glycine, alanine) neutralized with sodium N-methylglycinate sold under the name Proteol SAV 50 S by the company SEPPIC (CTFA name: sodium cocoyl amino acids).

b) Examples of phosphates and (C6-C30)alkyl phosphates that may be mentioned include mono(C6-C30)alkyl phosphates and di(C6-C30)alkyl phosphates, such as the lauryl monophosphate sold under the name MAP 20® by the company Kao Chemicals, the potassium salt of dodecylphosphoric acid, the mixture of monoester and diester (predominantly diester) sold under the name Crafol AP-31® by the company Cognis, the mixture of octylphosphoric acid monoester and diester sold under the name Crafol AP-20® by the company Cognis, the mixture of ethoxylated (7 mol of EO) phosphoric acid monoester and diester of 2-butyloctanol, sold under the name Isofol 12 7 EO-Phosphate Ester® by the company Condea, the potassium or triethanolamine salt of mono($C_{12}$-$C_{13}$)alkyl phosphate sold under the references Arlatone MAP 230K-40® and Arlatone MAP 230T-60® by the company Uniqema, the potassium lauryl phosphate sold under the name Dermalcare MAP XC-99/09® by the company Rhodia Chimie, and the potassium cetyl phosphate sold under the name Arlatone MAP 160K by the company Uniqema.

c) As carboxylates, mention may be made of:
(C6-C24)alkyl ether carboxylates, preferably (C12-C20) alkyl ether carboxylates;
(C6-C24)alkyl(amido) ether carboxylates (AEC), in particular those comprising from 2 to 50 alkylene oxide and in particular ethylene oxide groups, such as the compounds sold by the company Kao under the name Akypo, such as sodium lauryl amido ether carboxylate (3 EO), sold under the name Akypo Foam 30® by the company Kao Chemicals;
The polyoxyalkylenated alkyl (amido) ether carboxylic acids that may be used are preferably chosen from those of formula (1):

$R_1$—$(OC_2H_4)_n$—$OCH_2COOA$     (1)

in which:
R1 represents a linear or branched C6-C24 alkyl or alkenyl radical, an alkyl(C8-C9)phenyl radical, a radical $R_2CONH$—$CH_2$—$CH_2$— with R2 denoting a linear or branched C9-C21 alkyl or alkenyl radical. Preferably, R1 is a C8-C20 and preferably C8-C18 alkyl radical, and aryl preferably denotes phenyl,
n is an integer or decimal number (average value) ranging from 2 to 24 and preferably from 2 to 10,
A denotes H, ammonium, Na, K, Li, Mg or a monoethanolamine or triethanolamine residue.

It is also possible to use mixtures of compounds of formula (1), in particular mixtures of compounds containing different groups R1.
The polyoxyalkylenated alkyl(amido) ether carboxylic acids that are particularly preferred are those of formula (1) in which:
R1 denotes a C12-C14 alkyl, cocoyl, oleyl, nonylphenyl or octylphenyl radical,
A denotes a hydrogen or sodium atom, and
n varies from 2 to 20 and preferably from 2 to 10.
Even more preferentially, use is made of compounds of formula (1) in which R denotes a C12 alkyl radical, A denotes a hydrogen or sodium atom and n ranges from 2 to 10;
polyoxyethylenated carboxylic acid salts, such as oxyethylenated (6 EO) sodium lauryl ether carboxylate (65/25/10 $C_{12-14-16}$), sold under the name Akypo Soft 45 NV® by the company Kao Chemicals, polyoxyethylenated and carboxymethylated fatty acids originating from olive oil, sold under the name Olivem 400® by the company Biologia E Tecnologia, or oxyethylenated (6 EO) sodium tridecyl ether carboxylate, sold under the name Nikkol ECTD-6NEX® by the company Nikkol;

d) (C6-C30) acyl or alkyl acids and alkali metal salts thereof, such as:
(C6-C30)acylsarcosinates, and preferably (C12-C28) acylsarcosinates, better still (C14-C24)acylsarcosinates or even better (C16-C22)acylsarcosinates, such as the sodium lauroyl sarcosinate sold under the name Sarkosyl NL 97® by the company Ciba or sold under the name Oramix L30® by the company SEPPIC, sodium myristoyl sarcosinate sold under the name Nikkol Sarcosinate MN® by the company Nikkol, and sodium palmitoyl sarcosinate sold under the name Nikkol Sarcosinate PN® by the company Nikkol,
(C6-C30)alkylcitrates, optionally oxyalkylenated, such as the oxyethylenated (9 mol) citric monoester of cocoyl alcohols sold under the name Witconol EC 1129 by the company Goldschmidt,
(C6-C30)alkylgalacturonates, such as the sodium dodecyl-D-galactoside uronate sold by the company Soliance.

e) Succinates may be chosen from alkylsulfosuccinates, alkyl ether sulfosuccinates, alkylamidesulfosuccinates, with alkyl groups of these compounds comprising from 6 to 30 carbon atoms, especially from 12 to 28, better still from 14 to 24 or even from 16 to 22 carbon atoms. Examples of sulfosuccinates that may be mentioned include lauryl sulfosuccinate, the oxyethylenated (3 EO) lauryl alcohol monosulfosuccinate (70/30 $C_{12}/C_{14}$) sold under the names Setacin 103 Special® and Rewopol SB-FA 30 K 4® by the company Witco, the disodium salt of a hemisulfosuccinate of $C_{12}$-$C_{14}$ alcohols, sold under the name Setacin F Special Paste® by the company Zschimmer Schwarz, the oxyethylenated (2 EO) disodium oleamidosulfosuccinate sold under the name Standapol SH 135® by the company Cognis, the oxyethylenated (5 EO) laurylamide monosulfosuccinate sold under the name Lebon A-5000® by the company Sanyo, the oxyethylenated (10 EO) disodium salt of lauryl citrate monosulfosuccinate sold under the name Rewopol SB CS 50® by the company Witco, and the ricinoleic monoethanolamide monosulfosuccinate sold under the name Rewoderm S 1333® by the company Witco. Polydimethylsiloxane sulfosuccinates may also be used, such as disodium PEG-12 dimethicone sulfosuccinate sold under the name Mackanate-DC30 by the company MacIntyre.

f) Mention may be made, as sulfates, of alkyl sulfates, alkyl ether sulfates, alkylamido ether sulfates, alkylaryl polyether sulfates, monoglyceride sulfates, the alkyl groups comprising 6 to 30 carbon atoms, preferably from 12 to 28, better still from 14 to 24 or even from 16 to 22 carbon atoms, and the aryl group preferably denoting a phenyl or benzyl group. The sulphate surfactant may be in the form of alkali metal or alkaline earth metal, ammonium or amino alcohol salt. As examples of (C6-C30)alkylsulfates, mention may be made of triethanolamine lauryl sulfate (CTFA name: TEA-lauryl sulfate), such as the product sold by the company Huntsman under the name Empicol TL40 FL or the product sold by the company Cognis under the name Texapon T42, which products are at 40% in aqueous solution. Mention may also be made of ammonium lauryl sulfate (CTFA name: ammonium lauryl sulfate), such as the product sold by the company Huntsman under the name Empicol AL 30FL, which is at 30% in aqueous solution. Mention may be made, as (C6-C30)alkyl ether sulfates, for example, of sodium lauryl ether sulfate (CTFA name: sodium laureth sulfate), such as that sold under the names Texapon N40 and Texapon AOS 225 UP by the company Cognis, or ammonium lauryl ether sulfate (CTFA name: ammonium laureth sulfate), such as that sold under the name Standapol EA-2 by the company Cognis.

g) Mention may be made as sulfonates of alkylsulfonates, alkylamidosulfonates, alkylarylsulfonates, α-olefinsulfonates, paraffin sulfonates, with alkyl groups comprising from 6 to 30 carbon atoms, especially from 12 to 28, better still from 14 to 24 or even from 16 to 22 carbon atoms; the aryl group preferably denoting a phenyl or benzyl group; these compounds possibly being polyoxyalkylenated, especially polyoxyethylenated, and then preferably comprising from 1 to 50 ethylene oxide units and better still from 2 to 10 ethylene oxide units, alkylsulfoacetates, and also the salts of these compounds. As examples of α-olefinsulfonates mention may be made of sodium α-olefinsulfonate (C14-C16), sold under the name Bio-Terge AS-40® by the company Stepan, sold under the names Witconate AOS Protégé® and Sulframine AOS PH 12® by the company Witco or sold under the name Bio-Terge AS-40 CG® by the company Stepan, secondary sodium olefinsulfonate, sold under the name Hostapur SAS 30® by the company Clariant; or linear alkylarylsulfonates, such as sodium xylenesulfonate, sold under the names Manrosol SXS30®, Manrosol SXS40® and Manrosol SXS93® by the company Manro.

h) Mention may be made, as isethionates, of acylisethionates comprising from 6 to 24, preferably from 12 to 18 carbon atoms, such as sodium cocoylisethionate, such as the product sold under the name Jordapon CI P® by the company Jordan.

i) Mention may be made, as taurates, of the sodium salt of palm kernel oil methyltaurate, sold under the name Hostapon CT Paté® by the company Clariant; N-acyl-N-methyltaurates, such as sodium N-cocoyl-N-methyltaurate, sold under the name Hostapon LT-SF® by the company Clariant or sold under the name Nikkol CMT-30-T® by the company Nikkol, or sodium palmitoyl methyltaurate, sold under the name Nikkol PMT® by the company Nikkol.

j) The anionic derivatives of (C6-C30)alkyl polyglucosides can in particular be citrates, tartrates, sulfosuccinates, carbonates and glycerol ethers obtained from alkyl polyglucosides. Mention may be made, for example, of the sodium salt of cocoylpolyglucoside (1,4) tartaric ester, sold under the name Eucarol AGE-ET® by the company Cesalpinia, the disodium salt of cocoylpolyglucoside (1,4) sulfosuccinic ester, sold under the name Essai 512 MP® by the company SEPPIC, or the sodium salt of cocoylpolyglucoside (1,4) citric ester, sold under the name Eucarol AGE-EC® by the company Cesalpinia.

Preferably, the additional anionic surfactant is chosen from (C6-C30)alkyl sulfates, (C6-C30)alkyl ether sulfates such as sodium lauryl ether sulfate, (C6-C30)acylisethionates, (C6-C30) acyl or alkyl acids, in particular and mixtures thereof.

Additional Amphoteric and Zwitterionic Foaming Surfactants

The composition may further comprise an amphoteric and zwitterionic surfactant that is different from the amphoteric surfactant chosen from betaines or (C8-C20)alkyl betaines, (C8-C20)alkylamido(C1-C6)alkylbetaines mentioned above.

The additional amphoteric and zwitterionic surfactants can be chosen, for example, sulfobetaines, (C8-C20)alkylsulfobetaines, (C8-C20)alkylamido(C1-C6)alkylsulfobetaines (C8-C20)alkylamphoacetates and (C8-C20)alkylamphodiacetates, and mixtures thereof.

Mention may be made, as sulfobetaines, of hydroxysultaines, cocamidopropyl hydroxysultaine, such as the product sold under the name Rewoteric AM CAS by the company Goldschmidt-Degussa or the product sold under the name Crosultaine C-50® by the company Croda.

The additional amphoteric surfactants that may be used in the invention may be optionally quaternized secondary or tertiary aliphatic amine derivatives, in which the aliphatic group is a linear or branched chain comprising from 8 to 22 carbon atoms, said amine derivatives containing at least one anionic group, for instance a carboxylate, sulfonate, sulfate, phosphate or phosphonate group.

Among the optionally quaternized secondary or tertiary aliphatic amine derivatives that may be used, mention may also be made of the products of respective structures (A1) and (A2) below:

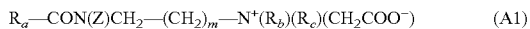

$$R_a\text{—CON(Z)CH}_2\text{—(CH}_2)_m\text{—N}^+(R_b)(R_c)(CH_2COO^-) \quad (A1)$$

in which:

$R_a$ represents a C10-C30 alkyl or alkenyl group derived from an acid $R_a$—COOH preferably present in hydrolysed coconut oil, a heptyl group, a nonyl group or an undecyl group, $R_b$ represents a β-hydroxyethyl group, $R_c$ represents a carboxymethyl group;

m is equal to 0, 1 or 2,

Z represents a hydrogen atom or a hydroxyethyl or carboxymethyl group;

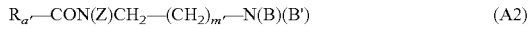

$$R_{a'}\text{—CON(Z)CH}_2\text{—(CH}_2)_{m'}\text{—N(B)(B')} \quad (A2)$$

in which:

B represents —CH$_2$CH$_2$OX', with X' representing —CH$_2$—COOH, CH$_2$—COOZ', CH$_2$CH$_2$—COOH, —CH$_2$CH$_2$—COOZ', or a hydrogen atom, B' represents —(CH$_2$)z-Y', with z=1 or 2, and Y' representing COOH, COOZ', CH$_2$—CHOH—SO$_3$H or —CH$_2$—CHOH—SO$_3$Z', m' is equal to 0, 1 or 2, Z represents a hydrogen atom or a hydroxyethyl or carboxymethyl group, Z' represents an ion resulting from an alkali or alkaline-earth metal, such as sodium, potassium or magnesium; an ammonium ion; or an ion resulting from an or-ganic amine and in particular from an amino alcohol, such as monoethanola-mine, diethanolamine and triethanolamine, monoisopropanolamine, diisopropa-nolamine or triisopropanolamine, 2-amino-2-methyl-1-propanol, 2-amino-2-methyl-1,3-propanediol and tris(hydroxymethyl) aminomethane, $R_{a'}$ represents a C10-C30 alkyl or alkenyl group of an acid $R_{a'}$COOH preferably pre-sent in hydrolysed linseed oil or coconut oil, an alkyl group, in particular a C17 alkyl group, and its iso form, or an unsaturated C17 group.

The compounds corresponding to formula (A2) are preferred.

Among the compounds corresponding to formula (A2) in which X' represents a hydrogen atom, mention may be made of compounds classified in the CTFA dictionary, under the names sodium cocoamphoacetate, sodium lauroamphoacetate, sodium caproamphoacetate and sodium capryloamphoacetate.

Other compounds corresponding to formula (A2) are disodium cocoamphodiacetate, disodium lauroamphodiacetate, disodium caproamphodiacetate, disodium capryloamphodiacetate, disodium cocoamphodipropionate, disodium lauroamphodipropionate, disodium caproamphodipropionate, disodium capryloamphodipropionate, lauroamphodipropionic acid and cocoamphodipropionic acid.

Examples that may be mentioned include the cocoamphodiacetate sold by the company Rhodia under the trade name Miranol® C2M Concentrate, the sodium cocoamphoacetate sold under the trade name Miranol Ultra C 32 and the product sold by the company Chimex under the trade name CHIMEXANE HA, the sodium cocoamphohydroxypropylsulfonate, sold under the name Miranol CSE by the company Rhodia.

Use may also be made of the compounds of formula (A3):

$$R_{a''}—NH—CH(Y'')—(CH_2)_n—C(O)—NH—(CH_2)_{n'}—N(R_d)(R_e) \quad (A3)$$

in which:
$R_{a''}$ represents a C10-C30 alkyl or alkenyl group of an acid $R_{a''}$—C(O)OH preferably present in hydrolysed linseed oil or coconut oil;
Y" represents the group —C(O)OH, —C(O)OZ", —CH$_2$—CH(OH)—SO$_3$H or the group CH$_2$—CH(OH)—SO$_3$—Z", with Z" representing a cationic counterion resulting from an alkali metal or alkaline-earth metal, such as sodium, an ammonium ion or an ion resulting from an organic amine;
$R_d$ and $R_e$ represent, independently of each other, a C1-C4 alkyl or hydroxyalkyl radical; and
n and n' denote, independently of each other, an integer ranging from 1 to 3.

Among the compounds corresponding to formula (A3), mention may in particular be made of the compound classified in the CTFA dictionary under the name sodium diethylaminopropyl cocoaspartamide, such as the one sold by the company Chimex under the name CHIMEXANE HB.

Preferably, the amphoteric or zwitterionic surfactant is chosen from (C8-C20)alkylamphoacetates such as sodium cocoamphoacetate, and mixtures thereof.

Nonionic Foaming Surfactant

The nonionic foaming surfactants that may be present in the composition of the invention may be chosen from alcohols, α-diols and (C1-20)alkylphenols, these compounds being polyethoxylated and/or polypropoxylated and/or polyglycerolated, the number of ethylene oxide and/or propylene oxide groups possibly ranging from 1 to 100, and the number of glycerol groups possibly ranging from 2 to 30; or alternatively these compounds comprising at least one fatty chain comprising from 8 to 30 carbon atoms and especially from 16 to 30 carbon atoms.

Mention may also be made of condensates of ethylene oxide and of propylene oxide with fatty alcohols; polyethoxylated fatty amides preferably having from 2 to 30 ethylene oxide units, polyglycerolated fatty amides comprising on average from 1 to 5, and in particular from 1.5 to 4, glycerol groups; ethoxylated fatty acid esters of sorbitan preferably containing from 2 to 40 ethylene oxide units, fatty acid esters of sucrose, polyoxyalkylenated and preferably polyoxyethylenated fatty acid esters containing from 2 to 150 mol of ethylene oxide, including oxyethylenated plant oils, N—(C6-24 alkyl)glucamine derivatives, amine oxides such as (C10-14 alkyl)amine oxides or N—(C10-14 acyl) aminopropylmorpholine oxides.

The non ionic surfactant may also be chosen from alkyl (poly)glycosides (APG), represented especially by the following general formula: $R_1O—(R_2O)_t-(G)_v$ in which:
R1 represents a linear or branched alkyl or alkenyl radical comprising 6 to 24 carbon atoms and especially 8 to 18 carbon atoms, or an alkylphenyl radical whose linear or branched alkyl radical comprises 6 to 24 carbon atoms and especially 8 to 18 carbon atoms;
R2 represents an alkylene radical comprising 2 to 4 carbon atoms,
G represents a sugar unit comprising 5 to 6 carbon atoms,
t denotes a value ranging from 0 to 10 and preferably 0 to 4,
v denotes a value ranging from 1 to 15 and preferably 1 to 4.

Preferably, the alkylpolyglycoside surfactants are compounds of the formula described above in which:
R1 denotes a linear or branched, saturated or unsaturated alkyl radical comprising from 8 to 18 carbon atoms,
R2 represents an alkylene radical comprising 2 to 4 carbon atoms,
t denotes a value ranging from 0 to 3 and preferably equal to 0,
G denotes glucose, fructose or galactose, preferably glucose;
the degree of polymerization, i.e. the value of v, possibly ranging from 1 to 15 and preferably from 1 to 4; the mean degree of polymerization more particularly being between 1 and 2.

The glycoside bonds between the sugar units are generally of 1-6 or 1-4 type and preferably of 1-4 type. Preferably, the alkyl(poly)glycoside surfactant is an alkyl(poly)glucoside surfactant. C8/C16 alkyl(poly)glycosides 1,4, and especially decyl glucosides and caprylyl/capryl glucosides, are most particularly preferred.

Among the commercial products, mention may be made of the products sold by the company COGNIS under the names PLANTAREN® (600 CS/U, 1200 and 2000) or PLANTACARE® (818, 1200 and 2000); the products sold by the company SEPPIC under the names ORAMIX CG 110 and ORAMIX NS 10; the products sold by the company BASF under the name LUTENSOL GD 70, or else the products sold by the company CHEM Y under the name AG10 LK.

Preferably, use is made of C8/C16-alkyl(poly)glycosides 1,4, especially as an aqueous 53% solution, such as those sold by Cognis under the reference Plantacare® 818 UP.

Preferentially, the nonionic surfactants are chosen from (C6-24 alkyl)polyglycosides, and more particularly (C8-18 alkyl)(poly)glycosides, ethoxylated C8-C30 fatty acid esters of sorbitan, polyethoxylated C8-C30 fatty alcohols and polyoxyethylenated C8-C30 fatty acid esters, these compounds preferably containing from 2 to 150 mol of ethylene oxide, and mixtures thereof.

The non ionic surfactant may also be chosen from oxyalkylenated glycerol esters. The oxyalkylenated glycerol esters are in particular the polyoxyethylenated derivatives of esters of glycerol and of a fatty acid and of their hydrogenated derivatives. These oxyalkylenated glycerol esters can be chosen, for example, from esters of glycerol and of fatty acids which are hydrogenated and oxyethylenated, such as PEG-200 hydrogenated glyceryl palmate, sold under the name Rewoderm LI-S 80 by the company Goldschmidt; oxyethylenated glycerol cocoates, such as PEG-7 glyceryl cocoate, sold under the name Tegosoft GC by the company Goldschmidt, and PEG-30 glyceryl cocoate, sold under the name Rewoderm LI-63 by the company Goldschmidt; and mixtures thereof.

The non ionic surfactant may also be chosen from oxyalkylenated sugar esters. The oxyalkylenated sugar esters are in particular polyethylene glycol ethers of fatty acid and sugar esters. These oxyalkylenated sugar esters can be chosen, for example, from oxyethylenated glucose esters, such as PEG-120 methyl glucose dioleate, sold under the name Glucamate DOE 120 by the company Amerchol.

According to a preferred embodiment of the invention, the nonionic surfactant is an alkyl polyglucoside which may be chosen especially from decylglucoside, caprylyl/capryl glucoside, laurylglucoside, cocoylglucoside and caprylylglucoside, and mixtures thereof.

Cationic Foaming Surfactant

According to one embodiment, the composition according to the invention may comprise at least one cationic surfactant, in particular in the case where it comprises an amphoteric foaming surfactant. The cationic surfactants that may be used according to the present invention are especially optionally polyoxyalkylenated primary, secondary or tertiary fatty amine salts, quaternary ammonium salts, imidazoline derivatives, and amine oxides of cationic nature, and mixtures thereof.

Examples of quaternary ammonium salts include:
those that have the general formula (IV) below:

(IV)

in which the radicals $R_1$ to $R_4$, which may be identical or different, represent a linear or branched aliphatic radical comprising from 1 to 30 carbon atoms or an aromatic radical, such as aryl or alkylaryl, at least one of the groups R8 to R11 containing from 8 to 30 carbon atoms and preferably from 12 to 24 carbon atoms. The aliphatic radicals may contain heteroatoms such as, in particular, oxygen, nitrogen, sulfur and halogen atoms. The aliphatic radicals are for example selected from (C1-C30)alkyl, (C1-C30) alkoxy, ($C_2$-$C_6$)polyoxyalkylene, (C1-C30)alkylamide, ($C_{12}$-$C_{22}$)alkyl($C_2$-$C_6$)alkylamido, ($C_{12}$-$C_{22}$)alkylacetate and (C1-C30)hydroxyalkyl radicals; $X^-$ is an anion chosen from the group consisting of halides, phosphates, acetates, lactates, ($C_1$-$C_6$)alkyl sulfates, and (C1-C4)alkylsulfonates or (C1-C4)alkylarylsulfonates. Preferably $R_1$ and $R_2$ denote a $C_1$-$C_4$ alkyl or a $C_1$-$C_4$ hydroxyalkyl.

quaternary ammonium salts of imidazolinium, for instance the salt of formula (V) below:

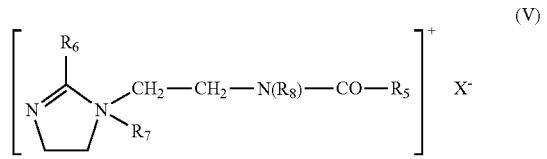

(V)

in which $R_5$ represents an alkenyl or alkyl radical containing from 8 to 30 carbon atoms, for example coconut or tallow fatty acid derivatives, $R_6$ represents a hydrogen atom, a $C_1$-$C_4$ alkyl radical or an alkenyl or alkyl radical containing from 8 to 30 carbon atoms, $R_7$ represents a $C_1$-$C_4$ alkyl radical, $R_8$ represents a hydrogen atom or a $C_1$-$C_4$ alkyl radical or an alkenyl or alkyl group comprising from 8 to 30 carbon atoms, $X^-$ is an anion chosen preferably from the group of halides, phosphates, acetates, lactates, (C1-C4) alkyl sulfates and (C1-C4)alkylsulfonates or (C1-C4)alkylaryl sulfonates. $R_5$ and $R_6$ preferably denote a mixture of alkenyl or alkyl radicals comprising from 12 to 21 carbon atoms, for example fatty acid derivatives of tallow, $R_7$ denotes methyl and $R_8$ denotes a hydrogen atom.

the quaternary di- or triammonium salts of formula (VI):

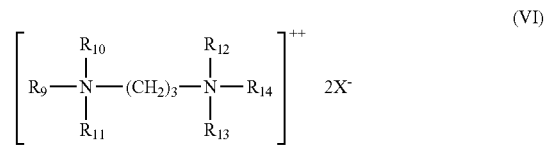

(VI)

in which $R_9$ denotes an alkyl radical containing approximately from 16 to 30 carbon atoms which is optionally hydroxylated and/or interrupted with one or more oxygen atoms, $R_{10}$ represents a hydrogen atom or an alkyl group containing from 1 to 4 carbon atoms or a group —$(CH_2)_3$—$N^+(R_{9a})(R_{10a})(R_{11a})$; wherein R9a, R10a, R11a, which may be identical or different, are chosen from hydrogen and an alkyl group comprising from 1 to 4 carbon atoms, $R_{11}$, $R_{12}$, $R_{13}$ and $R_{14}$, which are identical or different, are selected from hydrogen or an alkyl radical containing from 1 to 4 carbon atoms, and $X^-$ is an anion selected from the group consisting of halides, acetates, phosphates, nitrates and (C1-C4)alkyl sulfates, (C1-C4)alkylsulfonates and (C1-C4)alkylarylsulfonates, in particular methyl sulfate and ethyl sulfate.

Such compounds are, for example, FINQUAT CT-P (Quaternium 89) and FINQUAT CT (Quaternium 75) sold by the company FINETEX.

quaternary ammonium salts comprising at least one ester function, for example those of formula (VII) below:

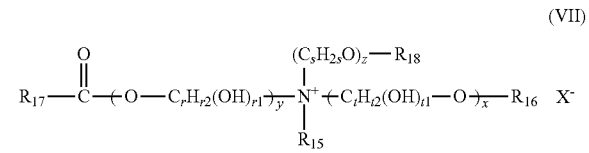

(VII)

in which:
$R_{15}$ is chosen from $C_1$-$C_6$ alkyl radicals and $C_1$-$C_6$ hydroxyalkyl or (C1-C6)dihydroxyalkyl radicals;
$R_{16}$ is chosen from:
the radical

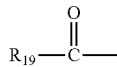

linear or branched, saturated or unsaturated $C_1$-$C_{22}$ hydrocarbon-based radicals $R_{20}$,
a hydrogen atom,
R18 is chosen from:
the radical

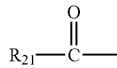

linear or branched, saturated or unsaturated $C_1$-$C_6$ hydrocarbon radicals R22, a hydrogen atom, R17, R19 and R21, which are identical or different, are chosen from linear or branched, saturated or unsaturated $C_7$-$C_{21}$ hydrocarbon radicals;

r, s and t, which may be identical or different, are integers ranging from 2 to 6;

r1 and t1, which may be identical or different, are equal to 0 or 1;

r2+r1=2 r and t1+t2=2 t;

y is an integer ranging from 1 to 10;

x and z, which may be identical or different, are integers ranging from 0 to 10;

$X^-$ is an anion;

with the proviso that the sum x+y+z is from 1 to 15, that when x is 0, then R16 denotes R20 and that when z is 0, then R18 denotes R22.

The alkyl radicals R15 may be linear or branched, and more particularly linear.

Preferably R15 denotes a methyl, ethyl, hydroxyethyl or dihydroxypropyl radical, and more particularly a methyl or ethyl radical.

Advantageously, the sum x+y+z is from 1 to 10.

When R16 is a hydrocarbon radical R20, it may be long and may have 12 to 22 carbon atoms, or may be short and may have from 1 to 3 carbon atoms.

When R18 is a hydrocarbon radical R22, it has preferably 1 to 3 carbon atoms.

Advantageously, R17, R19 and R21, which may be identical or different, are chosen from linear or branched, saturated or unsaturated $C_{11}$-$C_{21}$ hydrocarbon-based radicals, and more particularly from linear or branched, saturated or unsaturated $C_{11}$-$C_{21}$ alkyl and alkenyl radicals.

Preferably, x and z, which may be identical or different, are equal to 0 or 1.

Advantageously, y is equal to 1.

Preferably r, s and t, which may be identical or different, are equal to 2 or 3, and more particularly are equal to 2.

The anion $X^-$ is preferably a halide, preferably chloride, bromide or iodide, or an (C1-C4)alkyl sulfate, more particularly methyl sulfate, or (C1-C4)alkyl sulfonate like methanesulfonate, (C1-C4)alkylaryl sulfonate, phosphate, nitrate, tosylate, an anion derived from an organic acid, such as acetate or lactate, or any other anion that is compatible with the ammonium containing an ester function.

The anion $X^-$ is even more particularly chloride, methyl sulphate or ethyl sulfate.

The ammonium salts more particularly used are those of formula (VII) in which:

R15 denotes a methyl or ethyl radical;

x and y are equal to 1;

z is equal to 0 or 1;

r, s and t are equal to 2;

R16 is chosen from:

the radical $R_{19}$—CO methyl, ethyl or $C_{14}$-$C_{22}$ hydrocarbon-based radicals, a hydrogen atom.

R18 is chosen from:

the radical $R_{21}$—CO a hydrogen atom.

R17, R19 and R21, which may be identical or different, are chosen from linear or branched, saturated or unsaturated $C_{13}$-$C_{17}$ hydrocarbon-based radicals, and preferably from linear or branched, saturated or unsaturated $C_{13}$-$C_{17}$ alkyl and alkenyl radicals.

The hydrocarbon-based radicals are advantageously linear.

Among the quaternary ammonium salts of formula (IV), preference is given, on the one hand, to tetraalkylammonium halides and preferably tetraalkylammonium chlorides, for instance dialkyldimethylammonium or alkyltrimethylammonium chlorides in which the alkyl radical contains approximately 12 to 22 carbon atoms, in particular behenyltrimethylammonium chloride, distearyldimethylammonium chloride, cetyltrimethylammonium chloride and benzyldimethylstearylammonium chloride, or else, on the other hand, to palmitylamidopropyltrimethylammonium halides, and preferably chloride or the stearamidopropyldimethyl (myristyl acetate)ammonium halides, and preferably chloride, such as the one sold under the name "Ceraphyl 70" by the company Van Dyk.

Examples of compounds of formula (VII) that may be mentioned include the diacyloxyethyldimethylammonium, diacyloxyethylhydroxyethylmethylammonium, monoacyloxyethyldihydroxyethylmethylammonium, triacyloxyethylmethylammonium and monoacyloxyethylhydroxyethyldimethylammonium salts (chloride or methyl sulfate in particular), and mixtures thereof. The acyl radicals preferably contain 14 to 18 carbon atoms and are obtained more particularly from a plant oil such as palm oil or sunflower oil. When the compound contains several acyl radicals, these radicals may be identical or different.

These products are obtained, for example, by direct esterification of triethanolamine, triisopropanolamine, an alkyldiethanolamine or an alkyldiisopropanolamine, which are optionally oxyalkylenated, with fatty acids or with fatty acid mixtures of plant or animal origin, or by transesterification of the methyl esters thereof. This esterification is followed by a quaternization using an alkylating agent such as an alkyl halide (preferably a methyl or ethyl halide), a dialkyl sulfate (preferably dimethyl or diethyl sulfate), methyl methanesulfonate, methyl para-toluenesulfonate, glycol chlorohydrin or glycerol chlorohydrin.

Such compounds are sold, for example, under the names Dehyquart by the company Cognis, Stepanquat by the company Stepan, Noxamium by the company CECA or Rewoquat WE 18 and Rewoquat W75 by the company Degussa.

The composition according to the invention may contain, for example, a mixture of quaternary ammonium monoester, diester and triester salts with a weight majority of diester salts. Use may also be made of the ammonium salts containing at least one ester function that are described in U.S. Pat. No. 4,874,554 and U.S. Pat. No. 4,137,180. Use may also be made of behenoylhydroxypropyltrimethylammonium chloride, for example, sold by the company KAO under the name QUARTAMIN BTC 131.

Preferably, the ammonium salts containing at least one ester function contain two ester functions.

Quaternary diammonium salts of formula (VI) that are suitable for the invention comprise, in particular, propanetallowdiammonium chloride.

Preferably, the cationic surfactants are chosen from the compounds of formula (VI) and the compounds of formula (VII), preferably from cetyltrimethylammonium, behenyltrimethylammonium, and dipalmitoylethylhydroxyethylmethylammonium salts, and mixtures thereof, and more particularly from behenyltrimethylammonium chloride or methosulfate, cetyltrimethylammonium chloride or methosulfate, and dipalmitoylethylhydroxyethylmethylammonium chloride or methosulfate, and mixtures thereof. Even more preferentially, the cationic surfactant is a behenyltrimethylammonium salt.

The surfactant system may further comprise at least one foaming surfactant chosen from anionic, amphoteric, non-ionic and/or cationic foaming surfactants, and mixtures thereof, the said anionic surfactant being in particular chosen from anionic derivatives of proteins of plant origin or of silk proteins, phosphates and (C6-C30)alkyl phosphates, (C6-C24)alkyl ether carboxylates, (C6-C24)alkyl(amido) ether carboxylates, (C6-C30)alkylsulfosuccinates, (C6-C30) alkyl ether sulfosuccinates, (C6-C30) alkylamidesulfosuccinates, (C6-C30) acyl or alkyl acids, (C6-C30)alkyl sulfates, (C6-C30)alkyl ether sulfates, (C6-C30)alkylamido ether sulfates, (C6-C30)alkylaryl polyether sulfates, monoglyceride sulfates, (C6-C30)alkylsulfonates, (C6-C30)alkylamidosulfonates, (C6-C30)alkylarylsulfonates, (C6-C30)α-olefinsulfonates, paraffin sulfonates, (C6-C24)acylisethionates, taurates, (C6-C30)alkyl sulfoacetates, polypeptides, anionic derivatives of (C6-C30)alkyl polyglucoside, and soaps (fatty acid salts), and mixtures thereof, more particularly from (C6-C30)alkyl sulfates, (C6-C30)alkyl ether sulfates, (C6-C24)acyl isethionates, (C6-C30) acyl or alkyl acids, and mixtures thereof, the said amphoteric or zwitterionic surfactant being in particular chosen from sulfobetaines, (C8-C20)alkylsulfobetaines, (C8-C20)alkylamido(C1-C6)alkylsulfobetaines, (C8-C20)alkylamphoacetates and (C8-C20) alkylamphodiacetates, more particularly from (C8-C20) alkylsulfobetaines, (C8-C20)alkylamphoacetates and mixtures thereof, and mixtures thereof and the said nonionic surfactant being in particular chosen from alkyl polyglucosides (APGs), oxyalkylenated glycerol esters and oxyalkylenated sugar esters, and mixtures thereof, more particularly from APGs, and the said cationic surfactant being in particular chosen from optionally polyoxyalkylenated primary, secondary or tertiary fatty amine salts, quaternary ammonium salts, quaternary ammonium salts of imidazolinium, and amine oxides of cationic nature, and mixtures thereof.

According to a particular embodiment, the composition according to the present invention is devoid of cationic surfactant.

Non Foaming Surfactant

The composition may further comprise a non foaming surfactant.

The non foaming surfactant may also be chosen among non-ionic foaming surfactants, and in particular mono-, di-, or tri-esters of (C6-C30) fatty acids and of (poly)glycerol and mixtures thereof, and in particular mono-, di-, or tri-esters of (C12-C24) fatty acids and of (poly)glycerol and mixtures thereof.

The fatty acid moiety of the ester of fatty acid and (poly)glycerol may be in particular chosen among lauric, myristic, palmitic, stearic, arachidic and behenic.

The mono-, di-, or tri-esters of (C6-C30) fatty acids and of (poly)glycerol may have from 1 to 10, preferably 1 to 6 glycerol units, and has preferably only one glycerol unit.

In particular, mention may be made of:
  glyceryl stearates, such as glyceryl monostearate, like the one sold under the name DUB GMS 50/50 by STEARINERIE DUBOIS or under the name BFP 74K FLAKES by the company CARAVAN INGREDIENTS; mixtures of glyceryl mono- and distearate, such as the product sold under the name TEGIN PELLETS by EVONIK GOLDSCHMIDT or the product sold under the name CERASYNT SD by the company ISP; glyceryl isostearate such as the product PECEOL ISOSTEARIQUE sold by GATTEFOSSE; mixures of glyceryl mono-, di- and tristearate like the one sold under the name LIPO GMS 450 V by the company LIPO CHEMICALS; polyglyceryl-2 diisostearate like the one sold under the name DERMOL DGDIS by the company ALZO; polyglyceryl-2 isostearate, like the one sold under the name SALACOS 41V by the company NISSHIN OILLIO; polyglyceryl-10 stearate, like the one sold under the name DECAGLYN 1-SV by the company NIKKO; polyglyceryl-2 triisostearate, like the one sold under the name COSMOL 43 N by the company NISSHIN OILLIO; polyglyceryl-4 isostearate like the one sold under the name ISOLAN GI 34 EVONIK GOLDSCHMIDT; polyglyceryl-3 isostearate, like the one sold under the name LAMEFORM TGI by the company COGNIS glyceryl laurates, such as polyglyceryl-10 laurate like the one sold under the name DERMOFEEL G 10 L by the company DR STRAETMANS; polyglyceryl-6 laurate like the one sold under the name NIKKOL HEXAGLYN 1 L by the company NIHON SURFACTANT; polyglyceryl-10 trilaurate like the one sold under the name SUNSOFT Q-123Y-C by the company TAIYO KAGAKU; polyglyceryl-2 laurate like the one sold under the name SUNSOFT Q-12D-C by the company TAIYO KAGAKU; polyglyceryl-5 laurate, like the one sold under the name SUNSOFT A-121E-C by the company TAIYO KAGAKU; a mixture of glyceryl mono and di-laurate, for example a 90/10 mixture of glyceryl mono- and di-laurate like the one sold under the name GRILLOMULS L-90 by the company GRILLO-WERKE or like the one sold under the name TEGIN L 90 by the company EVONIK; polyglyceryl-3 laurate like the one sold under the name TRIGLYCERIN-MONOLAURAT by the company SAFIC-ALCAN; glyceryl monolaurate, like the one sold under the name GML by the company HENAN ZHENGTONG CHEMICAL or under the name SUNSOFT NO.750-C by TAIYO KAGAKU;

glyceryl myristates, such as polyglyceryl-2 myristate, like the one sold under the name SUNSOFT Q-14D-C by the company TAIYO KAGAKU; polyglyceryl-5 trimyristate, like the one sold under the name SUNSOFT A-143E-C by the company TAIYO KAGAKU; polyglyceryl-5 myristate, like the one sold under the name SUNSOFT A-141E-C by the company TAIYO KAGAKU; polyglyceryl-10 myristate like the one sold under the name SUNSOFT Q-14Y-C by the company TAIYO KAGAKU; polyglyceryl-6 myristate, like the one sold under the name NIKKOL HEXAGLYN 1-M sold by NIKKO;

glyceryl palmitates, such as polyglyceryl-2 palmitate like the one sold by SAKAMOTO YAKUHIN; polyglyceryl-3 palmitate like the one sold under the name DERMOFEEL PP by the company DR STRAETMANS; polyglyceryl-10 dipalimitate, like the one sold under the name POLYALDO 10-2-P K FG by the company LONZA;

glyceryl behenates, such as glyceryl dibehenate like the one sold under the name COMPRITOL E ATO by the company GATTEFOSSE; polyglyceryl-6 behenate like the one sold under the name PELEMOL 6G22 by the company PHOENIX CHEMICAL; mixures of glyceryl mono-, di- and tribehenate, like the one sold under the name BEHENATE DE GLYCEROL WL 251 by the company GATTEFOSSE and mixtures thereof.

As non foaming surfactant, mention may also be made of lecithin.

Lecithin according to the invention may be from soya, sunflower, egg and mixtures thereof. In a particular embodiment, the lecithin is from soya, like the one sold under the name EMULMETIK 100 J by the company CARGILL.

In a particular embodiment, the non foaming surfactant is chosen among (C8-C20) fatty acids, mono-, di-, or tri-esters of (C6-C30) fatty acids and of (poly)glycerol, lecithins and mixtures thereof.

In a particular embodiment, non foaming surfactants are chosen among lauric acid, glyceryl monostearate, glyceryl distearate, lecithin, and mixtures thereof.

According to a preferred embodiment of the invention, the composition comprises:
- a surfactant system comprising (i) at least one N—(C6-C30)acyl-amino based surfactant, (ii) at least one amphoteric surfactant chosen from betaines or (C8-C20)alkyl betaines, (C8-C20)alkylamido(C1-C6)alkylbetaines, and mixtures thereof and (iii) a salt of $C_8$-$C_{20}$ fatty acid, preferably respectively chosen from potassium cocoyl glycinate, lauryl betaine or coco betaine and potassium cocoate, the said surfactant system being advantageously included in a content ranging from 5 to 12% by weight relative to the total weight of the composition, for example ranging from 7 to 11% by weight;
- at least non associative crosslinked copolymer of (meth)acrylic acid, and of (C1-C4)alkyl esters thereof, preferably chosen from a crosslinked copolymer of vinyl neodecanoate and one or more monomers of acrylic acid, methacrylic acid or one of their (C1-C4)alkyl esters crosslinked with an allyl ether of trimethylolpropane or pentaerythritol, a crosslinked copolymer of acrylic acid and/or methacrylic acid and an ester thereof comprising less than 6 carbon atoms, preferably (C1-C4)alkyl ester thereof, and a crosslinked copolymer comprising at least one methacrylic unit and at least one $C_1$-$C_4$ alkyl acrylate unit, for example a ethyl acrylate unit, the said non associative crosslinked copolymer of (meth)acrylic acid, and of (C1-C4) alkyl esters thereof being advantageously included in the composition in an active material content ranging from 2 to 4% by weight, in particular from 2.2 to 3.6% by weight, and more particularly from 2.4 to 3.2% by weight, with respect to the total weight of the composition.

Polyols

According to a particular embodiment, the composition according to the present invention further comprises at least one polyol or a mixture of polyols.

For the purpose of the present invention, the term "polyol" should be understood to mean any organic molecule comprising at least two free hydroxyl groups.

A polyol suitable for the invention may be a compound such as a saturated or unsaturated, linear, branched or cyclic alkyl bearing, on the alkyl chain, at least two —OH functions, in particular at least three —OH functions, and more particularly at least four —OH functions.

The polyols advantageously suitable for the formulation of the foaming cleanser composition according to the present invention are those having, in particular, from 2 to 20 preferably 2 to 16 carbon atoms, preferably 2 to 10, preferably 3 to 8 carbon atoms.

Among polyols, the following may be cited: glycerine, 1,3-propanediol, isoprene glycol, pentylene glycol, hexylene glycol, glycols such as ethylene glycol, propylene glycol, butylene glycol, diethylene glycol and dipropylene glycol, polyglycerols with 2 to 6 repeating units, for instance diglycerol, erythritol, arabitol, adonitol, sorbitol, dulcitol, glucose, fructose, xylose, trehalose, sucrose, maltose, saccharose and lactose, and mixtures thereof.

According to a particular embodiment of the present invention, the polyol is not a polymer with repeating units.

According to a preferred embodiment, the polyol is glycerine.

Oxyethylenated Polymers

The composition according to the invention may also comprise oxyethylenated polymers. The oxyethylenated polymers that may be used in the composition of the invention are those with a molecular weight (MW) calculated by weight of greater than or equal to 300 000, the molecular weight preferably ranging from 400 000 to $4\times10^6$ and better still from 500 000 to $2\times10^6$.

According to one preferred embodiment of the invention, the oxyethylenated polymer is a compound of formula (A):

$$H(OCH_2CH_2)_nOH \qquad (A)$$

in which n is an integer ranging from 7000 to 90 000, preferably from 10 000 to 75 000, more preferably from 25 000 to 65 000, even more preferably from 35 000 to 55 000.

As oxyethylenated polymer preferably used in the composition of the invention, mention may be made especially of PEG 14M (formula (A) in which n is 14 000) such as the product sold under the name Polyox WSR 205 by the company Amerchol, PEG-45M (formula (A) in which n is 45 000) such as the product sold under the name Polyox WSR N-60 K by the company Amerchol, PEG-90M (formula (A) in which n is 90000) such as the product sold under the name POLYOX WSR 301 by the company Dow Chemical and mixtures thereof.

According to a particular embodiment of the present invention, the oxyethylenated polymer is PEG-45M, in particular as sold under the name POLYOX WSR N 60 K by Dow Chemical.

According to a particular embodiment of the present invention, the oxyethylenated polymer is PEG-90M, in particular as sold under the name POLYOX WSR 301 by Dow Chemical.

The oxyethylenated polymer may be present in the composition of the invention in an amount preferably ranging from 0.001% to 5% by weight and better still from 0.005% to 3% by weight, and even more preferably from 0.01% to 1% by weight, relative to the total weight of the composition.

Fillers

"Fillers" should be understood as meaning solid particles which are insoluble in the medium of the composition, whatever the temperature at which the composition is manufactured.

The fillers can be colourless or white and inorganic or organic, of any physical shape (platelet, spherical, lamellar or oblong) and of any crystallographic form (for example sheet, cubic, hexagonal, orthorhombic and the like). The fillers can be porous or nonporous.

Mention may be made, as fillers, of inorganic fillers, such as silica, hydrated silica, microcrystalline cellulose, polyolefin particle, perlite, clays, ceramic beads, calcium carbonate, titanium oxides, talc or magnesium silicate (for example of particle size of 5 microns), like the one sold under the name Luzenac 15 M00® by Luzenac or talcs sold under the names Luzenac 00 and Luzenac Pharma M by Luzenac, kaolin or aluminium silicate, such as, for example, that sold under the name Kaolin Supreme® by Imerys, or sand with a particle size of between 1 and 1000 microns, or organic fillers, such as starches, such as, for example, the product sold under the name Mais Starch B® by Roquette, maize starch, Natpure Hollow Bead or Cellulobead D-10 spheres, Nylon microspheres, such as those sold under the name Orgasol 2002 UD NAT COS® by Atochem, microspheres based on vinylidene chloride/acrylonitrile/methacrylonitrile copolymer including isobutane, expanded microspheres, such as those sold under the name Expancel 551 DE® by Expancel, micronized or nonmicronized plant powders, such as the fruit powders from Lessonia or bamboo powders, or rice grain husk powder, polytetrafluoroethylene powders; acrylic copolymer powders; polyethylene powders; polyamide powders; and their mixtures.

Mention may also be made, as fillers, of exfoliating particles which will make possible scrubbing of the skin. Use may be made, as exfoliating particles, of exfoliating or scrubbing particles of mineral, vegetable or organic origin. Thus, use may be made, for example, of polyethylene beads or powder, such as those sold under the name Microthene MN 727 or Microthene MN 710-20 by Equistar or such as the powders sold under the name Gotalene 120 Colorless 2 by Dupont; Nylon particles, such as those sold by Arkema under the name Orgasol 2002 Exd Nat Cos; poly(vinyl chloride) powder, pumice (INCI name) such as pumice 3/B from Eyraud; ground fruit kernel shells, such as ground materials derived from apricot kernels or walnut shells; sawdust, wood flour or cork flour, glass beads; alumina (aluminium oxide) (INCI name: Alumina), such as the product sold under the name Dermagrain 900 by Marketech International; sugar crystals; beads which melt during application on the skin, such as, for example, spheres based on mannitol and cellulose which are sold under the Unisphere names by Induchem, agar-based capsules which are sold under the Primasponge names by Cognis and spheres based on jojoba esters which are sold under the Floraspheres names by Floratech; and their mixtures.

According to a particular embodiment of the present invention, the filler is chosen among thickening inorganic particles or organic particles.

Anti-shine effect and matifying effect may be provided by the presence within the composition according to the invention, of such particles.

Among non-thickening inorganic particles providing an anti-shine effect and/or matifying effect may be cited the following: talc, perlite, kaolin, silica, hydrated silica, and mixtures thereof.

According to a preferred embodiment of the present invention, suitable anti-shine and/or anti-matifying inorganic particles may be talc, in particular with a mean size below 30 µm.

According to other preferred embodiments of the present invention, kaolin (also called China clay) and perlite are suitable inorganic particles with anti-shine and/or matifying effect.

Among non-thickening organic particles with anti-shine and/or anti-matifying effect may be cited the following: polytetrafluoroethylene powders; acrylic copolymer powders; polyethylene powders; polyamide powders; and mixtures thereof.

According to one embodiment, the fillers are present in the composition according to the invention in a content ranging from 1 to 20% in weight, in particular from 2 to 15% in weight, and more particularly from 3 to 10% in weight, relative to the total weight of the composition.

Triglyceride Oil

According to a particular embodiment of the present invention, the composition may further comprise at least one triglyceride oil.

The presence of said triglyceride oil may be of particular interest to provide a moisturizing effect or emollient effect after washing the keratin material, in particular skin.

The triglyceride oil which is suitable for the present invention is preferably of plant origin.

The triglyceride oil is selected from an oil, a butter, and mixtures thereof.

Among the oil, the following may be cited: jojoba oil, babassu oil, sunflower oil, olive oil, canola oil, coconut oil, meadowfoam seed oil; Brazil nut oil, marula oil, maize oil, argan oil, soybean oil, marrow oil, grapeseed oil, linseed oil, sesame oil, hazelnut oil, apricot oil, *macadamia* oil, arara oil, coriander oil, castor oil, avocado oil, shea butter oil and rapeseed oil and copra oil.

Among the butter, the following may be cited: shea butter, Nilotica shea butter (*Butyrospermum parkii*), galam butter (*Butyrospermum parkii*), Borneo butter or fat or tengkawang tallow (*Shorea stenoptera*), *shorea* butter, illipe butter, *madhuca* butter or (*Bassia*) *Madhuca longifolia* butter, mowrah butter (*Madhuca latifolia*), katiau butter (*Madhuca mottleyana*), phulwara butter (*M. butyracea*), mango butter (*Mangifera indica*), murumuru butter (*Astrocaryum murumuru*), kokum butter (*Garcinia indica*), ucuuba butter (*Virola sebifera*), tucuma butter, painya (kpangnan) butter (*Pentadesma butyracea*), coffee butter (*Coffea arabica*), apricot butter (*Prunus armeniaca*), macadamia butter (*Macadamia ternifolia*), grapeseed butter (*Vitis vinifera*), avocado butter (*Persea gratissima*), olive butter (*Olea europaea*), sweet almond butter (*Prunus amygdalus dulcis*), cocoa butter (*Theobroma cacao*) and sunflower butter.

More preferably, the triglyceride oil is selected from sheabutter, olive oil, meadowfoam seed oil and canola oil, and still more preferably is sheabutter.

Said triglyceride oil may be present in the composition according to the present invention in an amount ranging from 0.1 to 30% in weight, in particular from 1 to 25% in weight, and more particularly from 2 to 20% in weight, relative to the total weight of the composition.

Additives

The composition according to the invention may contain various water-soluble or liposoluble additives, chosen from those conventionally used in skincare or makeup-removing products, insofar as these additives and the amounts thereof do not harm the qualities desired for the composition according to the invention.

The cleansing composition in accordance with the present invention may thus comprise the following additives: cosurfactants; oil; preserving agents; sequestrants (EDTA and salts thereof); antioxidants; fragrances; dyestuffs; encapsulated or non-encapsulated pigments or soluble dyes; hydrophilic or lipophilic, anionic, nonionic, cationic or amphoteric, thickening or dispersing polymers.

The amounts of these various adjuvants are those conventionally used in the field under consideration, for example from 0.01% to 20% of active material of the total weight of the composition. These adjuvants and the amounts thereof should be such that they do not modify the property desired for the composition of the invention.

The composition may also comprise a polymeric quaternary ammonium salt (other than the preceding surfactants).

These compounds are conditioning agents, i.e. they increase the amount of foam and produce a comfortable sensation of softness on the skin (moisturization maintenance).

The polymeric quaternary ammonium salts are cationic or amphoteric polymers containing at least one quaternized nitrogen atom. Polymeric quaternary ammonium salts that may especially be mentioned include the Polyquaternium products (CTFA name), which afford softness and creaminess to the foaming cream. These polymers may preferably be chosen from the following polymers:

Polyquaternium 5, such as the product Merquat 5 sold by the company Nalco;

Polyquaternium 6, such as the product Salcare SC 30 sold by the company Ciba, and the product Merquat 100 sold by the company Nalco;

Polyquaternium 7, such as the products Merquat S, Merquat 2200 and Merquat 550 sold by the company Nalco, the product Salcare SC 10 sold by the company Ciba and the product MERQUAT 7SPR POLYMER sold by Lubrizol;

Polyquaternium 10, such as the product Polymer JR400 sold by the company Amerchol;

Polyquaternium 11, such as the products Gafquat 755, Gafquat 755N and Gafquat 734 sold by the company ISP;

Polyquaternium 15, such as the product Rohagit KF 720 F sold by the company Röhm;

Polyquaternium 16, such as the products Luviquat FC905, Luviquat FC370, Luviquat HM552 and Luviquat FC550 sold by the company BASF;

Polyquaternium 22, such as the product Merquat 280 sold by the company Nalco;

Polyquaternium 28, such as the product Styleze CC10 sold by the company ISP;

Polyquaternium 39, such as the products Merquat Plus 3330 and Merquat 3330PR sold by the company Lubrizol;

Polyquaternium 44, such as the product Luviquat Care sold by the company BASF;

Polyquaternium 46, such as the product Luviquat Hold sold by the company BASF;

Polyquaternium 47, such as the product Merquat 2001 sold by the company Nalco.

Preferably, the quaternary ammonium salts are chosen from Polyquaternium-7, Polyquaternium-10, Polyquaternium-39 and Polyquaternium-47, and mixtures thereof.

The polymeric quaternary ammonium salts may be in an (active material) amount ranging, for example, from 0.01% to 5% by weight and better still from 0.05% to 1% by weight relative to the total weight of the composition.

As an example of a particular conditioning agent, mention may be made of Polyquaternium-39, sold especially by the company Nalco under the names Merquat Plus 3330 and Merquat 3330PR.

Composition

The composition according to the invention comprises an aqueous medium or aqueous phase, i.e. a medium comprising an amount of water of at least 50% by weight, preferably ranging from 50% to 95% by weight and better still from 60% to 90% by weight relative to the total weight of the composition.

The aqueous phase of the compositions according to the invention may contain, besides water, one or more water soluble solvents at room temperature (25° C.), such as for example linear or branched monoalcohols comprising from 1 to 6 carbon atoms like ethanol, propanol, butanol, isopropanol, isobutanol, pentanol, hexanol, and polyols with 2 to 20 carbon atoms as described above, and mixtures thereof.

In a particular embodiment the monoalcohol is ethanol.

When they are present, the amount of monoalcohols and of polyols in the composition of the invention may range, for example, from 0.01% to 30% by weight, preferably from 2% to 25% by weight and better still from 4% to 20% by weight relative to the total weight of the composition.

Throughout the description, including the claims, the expression "comprising a" should be understood as being synonymous with "comprising at least one", unless otherwise specified.

The expressions "between . . . and . . . " and "ranging from . . . to . . . " should be understood as meaning limits included, unless otherwise specified.

The examples that follow illustrate the present invention without limiting the scope thereof.

The examples were prepared according to the following process:

An aqueous phase was firstly prepared (with the N(C6-C30)acyl amino based surfactant (Amilite GCK-12H®), the amphoteric surfactant (lauryl betaine or coco betaine), glycerine and KOH) and heated around 60° C. The copolymer according to the present invention is then added into the water phase and mixed well. Afterwards, the mixture is cooled to 40° C. and then optional oil or talc may be added if present in the final composition.

Ingredient amounts are indicated in the following examples in active material weight percentages "% wgt".

EXAMPLE 1: FOAMING COMPOSITIONS FOR SKIN WASH a) Compositions 1A, 1B, 1C, 1D, 1E, 1F and 1G According to Invention

| Components INCI names | 1A % wgt | 1B % wgt | 1C % wgt | 1D % wgt | 1E % wgt | 1F % wgt | 1G % wgt |
|---|---|---|---|---|---|---|---|
| Potassium cocoyl glycinate + potassium cocoate (30% in water) sold under the name Amilite GCK-12H ® by Ajinomoto, cocoyl glycinate:soap = 19:11) | 6 (3.8:2.2) | 6 (3.8:2.2) | 6 (3.8:2.2) | 6 (3.8:2.2) | 6 (3.8:2.2) | 6 (3.8:2.2) | 6 (3.8:2.2) |
| Lauryl betaine | 2.2 | 2.2 | 2.2 | 2.2 | 2.2 | — | — |
| coco betaine | — | — | — | — | — | 2.2 | 2.2 |
| Glycerin | 10 | 10 | 10 | 10 | 10 | — | — |

-continued

| Components INCI names | 1A % wgt | 1B % wgt | 1C % wgt | 1D % wgt | 1E % wgt | 1F % wgt | 1G % wgt |
|---|---|---|---|---|---|---|---|
| PEG-45M (POLYOX WSR N 60K, by Dow Chemical) | — | — | — | — | — | 0.2 | — |
| Acrylate/vinyl neodecanoate crosspolymer sold under the name Aculyn 38 ® by Dow Chemical | 3 | 3 | — | — | 3 | 3 | 3 |
| Acrylates copolymer sold under the name Aculyn 33 ® by Dow Chemical | — | — | 3 | — | — | | |
| Acrylates copolymer sold under the name Carbopol Aqua SF-1 ® by Lubrizol | — | — | — | 3 | — | | |
| Polyquaternium-7 (MERQUAT 7SPR POLYMER by Lubrizol) | — | — | — | — | 0.1 | — | — |
| Poly quaternium-39 MERQUAT 3330PR POLYMER by Lubrizol) | 0.5 | 0.5 | 0.5 | 0.5 | 0.5 | 0.5 | 0.5 |
| KOH | q.s. | q.s. | q.s. | q.s. | q.s. | q.s. | q.s. |
| water | q.s. 100 | q.s. 100 | q.s. 100 | q.s. 100 | q.s. 100 | q.s. 100 | q.s. 100 |
| Total surfactant (%) | 8.2 | 8.2 | 8.2 | 8.2 | 8.2 | 8.2 | 8.2 |
| pH | 7.7 | 6.6 | 7.4 | 7.9 | 8.4 | 7.7 | 7.7 |

Compositions A, B, C, D, E, F and G provide satisfactory foam quality while achieving skin mildness when applied on skin.

b) Comparative Composition 1.1 Versus Composition 1A According to Invention

Comparative composition 1 comprises 16.4% by weight in active material of surfactants whereas composition A according to invention comprises 8.2% by weight in active material of surfactants.

| Components INCI names | Comparative Composition 1.1 % wgt |
|---|---|
| Potassium cocoyl glycinate + potassium cocoate (30% in water) sold under the name Amilite GCK-12H ® by Ajinomoto, cocoyl glycinate:soap = 19:11) | 12 (7.6:4.4) |
| Lauryl betaine | 4.4 |
| Glycerin | 10 |
| Acrylate/vinyl neodecanoate crosspolymer sold under the name Aculyn 38 ® by Dow Chemical | 3 |
| Polyquaternium-39 (MERQUAT 3330PR POLYMER by Lubrizol) | 0.5 |
| KOH | q.s. |
| water | q.s. 100 |
| Total surfactant (%) | 16.4 |
| pH | 7.7 |

The foaming quality and density of composition A according to the present invention having a low surfactant level are comparable to those of comparative composition 1 which has a larger amount of surfactants.

This result is quite amazing since, in general, it is expected that a composition containing a higher surfactant ratio gives more foam volume and density.

Thus, composition 1 according to the invention allows achieving completely satisfying quality and density foaming properties even at lesser amount of surfactant system.

EXAMPLE 2: ANTI-SHINE FOAMING COMPOSITIONS a) Compositions 2A, 2B, 2C, 2D, 2E and 2F According to Invention

| Components INCI names | 2A % wgt | 2E % wgt | 2C % wgt | 2D % wgt | 2E % wgt | 2F % wgt |
|---|---|---|---|---|---|---|
| Potassium cocoyl glycinate + potassium cocoate (30% in water) sold under the name Amilite GCK-12H ® by Ajinomoto | 6 (3.8:2.2) | 6 (3.8:2.2) | 6 (3.8:2.2) | 6 (3.8:2.2) | 6 (3.8:2.2) | 6 (3.8:2.2) |
| Lauryl betaine | 2 | 2 | 2 | 2 | 2 | 2 |
| Glycerin | 10 | 10 | 10 | 10 | 10 | 10 |

-continued

| Components INCI names | 2A % wgt | 2E % wgt | 2C % wgt | 2D % wgt | 2E % wgt | 2F % wgt |
|---|---|---|---|---|---|---|
| Acrylate/vinyl neodecanoate crosspolymer sold under the name Aculyn 38 ® by Dow Chemical | 2.7 | 2.55 | — | — | 3 | 3 |
| Acrylates copolymer sold under the name Aculyn 33 ® by Dow Chemical | — | — | 2.9 | — | — | — |
| Acrylates copolymer sold under the name Carbopol Aqua SF-1 ® by Lubrizol | — | — | — | 3 | — | — |
| Polyquaternium-39 (MERQUAT 3330PR POLYMER by Lubrizol) | 0.5 | 0.5 | 0.5 | 0.5 | 0.5 | 0.5 |
| Talc | 5 | 10 | 10 | 10 | — | — |
| Kaolin | — | — | — | — | 5 | — |
| Perlite | — | — | — | — | — | 5 |
| KOH | q.s. | q.s. | q.s. | q.s. | q.s. | q.s. |
| water | q.s. 100 | q.s. 100 | q.s. 100 | q.s. 100 | q.s. 100 | q.s. 100 |

Compositions 2A, 2B, 2C, 2D, 2E and 2F provide satisfactory foam quality while achieving skin mildness and anti-shine effect when applied on skin.

b) Comparative Composition 2.1 Versus Composition 2A According to Invention

Comparative composition 2.1 does not comprise non-associative crosspolymer whereas composition 2A according to invention comprises 2.7% of acrylates/vinyl Neodecanoate Crosspolymer (sold under the name Aculyn 38® by Dow Chemical).

| Components INCI names | Comparative Composition 1 % wgt |
|---|---|
| Potassium cocoyl glycinate + potassium cocoate (30% in water) sold under the name Amilite GCK-12H ® by Ajinomoto, cocoyl glycinate:soap = 19:11) | 6 (3.8:2.2) |
| Lauryl betaine | 2 |
| Glycerin | 10 |
| Polyquaternium-39 (MERQUAT 3330PR POLYMER by Lubrizol) | 0.5 |
| Talc | 5 |
| KOH | q.s. |
| water | q.s. 100 |

Comparative composition 2.1 does not provide any matifying effect but only a good foam quality.

Thus, the presence of both a non-associative copolymer according to the invention and talc in a composition according to the invention allows achieving both anti-shine effect when applied on skin and satisfactory foam quality.

EXAMPLE 3: MOISTURIZING FOAMING COMPOSITIONS a) Compositions 3A, 3B, 3C, 3D, 3E, 3F and 3G According to Invention

| Components INCI names | 3A | 3B | 3C | 3D | 3E | 3F | 3G | 3H | 3I |
|---|---|---|---|---|---|---|---|---|---|
| Potassium cocoyl glycinate + potassium cocoate (30% in water) sold under the name Amilite GCK-12H ® by Ajinomoto, cocoyl glycinate:soap = 19:11) | 7 (4.4:2.6) | 6 (3.8:2.2) | 6 (3.8:2.2) | 6 (3.8:2.2) | 6 (3.8:2.2) | 6 (3.8:2.2) | 6 (3.8:2.2) | 6 (3.8:2.2) | 6 (3.8:2.2) |
| Coco betaine | 3.3 | — | — | — | — | — | — | 2.2 | 2.2 |
| Lauryl betaine | — | 2.2 | 2.2 | 2.2 | 2.2 | 2.2 | 2.2 | — | — |
| Glycerin | 10 | 10 | 10 | 10 | 10 | 10 | 10 | 10 | 10 |
| Acrylate/vinyl neodecanoate crosspolymer sold under the name Aculyn 38 ® by Dow Chemical | 2.4 | 2.4 | 2.4 | 2.4 | 3 | — | — | 2.4 | 2.4 |
| Acrylates copolymer sold under the name Aculyn 33 ® by Dow Chemical | — | — | — | — | — | 3 | — | — | — |

-continued

| Components INCI names | 3A | 3B | 3C | 3D | 3E | 3F | 3G | 3H | 3I |
|---|---|---|---|---|---|---|---|---|---|
| Acrylates copolymer sold under the name Carbopol Aqua SF-1 ® by Lubrizol | — | — | — | — | — | — | 3 | — | — |
| Polyquaternium-7 (MERQUAT 7SPR POLYMER by Lubrizol) | 0.1 | — | — | — | — | — | — | — | — |
| Polyquaternium-39 (MERQUAT 3330PR POLYMER by Lubrizol) | 0.45 | 0.5 | 0.5 | 0.5 | 0.5 | 0.5 | 0.5 | 5 | 0.5 |
| Sheabutter | 10 | 10 | 20 | — | — | 10 | 10 | 10 | 10 |
| Olive oil | — | — | — | 10 | — | — | — | — | — |
| Canola oil | — | — | — | — | 10 | — | — | — | — |
| PEG-90M (POLYOX WSR 301 by Dow Chemical) | — | — | — | — | — | — | — | 0.1 | — |
| PEG-45M (POLYOX WSR N 60K by Dow Chemical) | — | — | — | — | — | — | — | — | 0.1 |
| mixture of glyceryl mono- and distearate (36/64) (TEGIN PELLETS by EVONIK GOLDSCHMIDT | — | — | — | — | — | — | — | 1 | 1 |
| lauric acid | — | — | — | — | — | — | — | 1.8 | 1.8 |
| KOH | q.s. | q.s. | q.s. | q.s. | q.s. | q.s. | q.s. | qs | qs |
| water | q.s. 100 | q.s. 100 | q.s. 100 | q.s. 100 | q.s. 100 | q.s. 100 | q.s. 100 | q.s. 100 | q.s. 100 |
| Total surfactant (%) | 10.3 | 8.2 | 8.2 | 8.2 | 8.2 | 8.2 | 8.2 | | |

Compositions 3A, 3B, 3C, 3D, 3E, 3F, 3G, 3H and 3I provide satisfactory foam quality while achieving skin mildness as well as a moisturizing effect and an emollient effect when applied on skin.

b) Comparative Composition 3.1 Versus Compositions 3B or 3C According to Invention Comparative composition 3.1 does not comprise sheabutter whereas compositions B and C comprise respectively 10% and 20% by weight of sheabutter relative to the total weight of the composition.

Thus, the presence of sheabutter in a composition according to the invention allows achieving moisturizing effect while maintaining a satisfactory foam quality.

c) Comparative Composition 3.2 Versus Composition 3E According to Invention

Comparative composition 3.2 does not comprise lauryl betaine whereas composition 3E comprises 2.2% by weight of lauryl betaine relative to the total weight of the composition.

| Components INCI names | Comparative Composition 1 % wgt |
|---|---|
| Potassium cocoyl glycinate + potassium cocoate (30% in water) sold under the name Amilite GCK-12H ® by Ajinomoto, cocoyl glycinate:soap = 19:11) | 6 (3.8:2.2) |
| Lauryl betaine | 2.2 |
| Glycerin | 10 |
| Acrylate/vinyl neodecanoate crosspolymer sold under the name Aculyn 38 ® by Dow Chemical | 2.4 |
| Polyquaternium-39 MERQUAT 3330PR POLYMER by Lubrizol) | 0.5 |
| KOH | q.s. |
| water | q.s. 100 |
| Total surfactant (%) | 8.2 |

Comparative composition 3.1 does not provide any moisturizing/emollient effect when applied on skin but only a good foam quality as compositions 3B or 3C according to the invention.

| Components INCI names | Comparative Composition 2 % wgt |
|---|---|
| Potassium cocoyl glycinate + potassium cocoate sold under the name Amilite GCK-12H ® by Ajinomoto, cocoyl glycinate:soap = 19:11) | 6 (3.8:2.2) |
| Glycerin | 10 |
| Acrylate/vinyl neodecanoate crosspolymer sold under the name Aculyn 38 ® by Dow Chemical | 2.4 |
| Polyquaternium-39 MERQUAT 3330PR POLYMER by Lubrizol | 0.5 |
| Canola oil | 10 |
| KOH | q.s. |
| water | q.s. 100 |
| Total surfactant (%) | 8.2 |

Comparative composition 3.2 does not provide a good foam quality as compositions E according to the invention.

Thus, the presence of lauryl betaine in a composition according to the invention allows achieving a satisfactory foam quality.

EXAMPLE 4: FOAM EXPERT PANEL TEST

Tests were performed to evaluate and compare the foam quality of an example according to the invention, i.e. composition 1A of example 1 versus comparative compositions 1.1 of example 1 such as already defined above.

Protocol

The invented example (composition 1A of example 1 above) was evaluated by a internal foam expert panels. The foam quality was compared between the composition 1A of example 1 versus the comparative composition 1.1 in example 1 given above.

Results and Conclusion: Composition 1A of Example 1 Versus Comparative Composition 1.1 of Example 1

The following table shows the profile of the foam quality evaluated by 16 internal experts. This table indicates that the attributes related to foam are identical to those of comparative composition 1.1 of example 1 even though comparative composition 1.1 of example 1 has two times more surfactant than composition 1A of example 1.

TABLE 1

|  | Foam density | Size of bubble | Foam homogeneity | Foam volume |
|---|---|---|---|---|
| composition A of example 1 | 12 | 2.14 | 11.58 | 7.16 |
| comparative composition 1 of example 1 | 11.71 | 2.27 | 11.84 | 7.14 |

In general, it is expected that a formula containing a higher surfactant ratio gives more foam volume and density. However, these results show that surfactant level is independent on foam volume and density in the claimed compositions.

EXAMPLE 5: IN VITRO KERATIN TEST

Tests were performed to evaluate and compare composition 1B of example 1 with the following comparative composition 5.1:

| Components INCI names | Comparative composition 5.1 % wgt |
|---|---|
| Stearic acid | 13 |
| Myristic acid | 1 |
| Lauric acid | 16 |
| Palmitic acid | 4 |
| Glyceryl stearate | 1 |
| Glycerin | 21 |
| Polyquaternium-7 MERQUAT 7SPR POLYMER by Lubrizol | 0.9 |
| KOH | q.s. |
| water | q.s. 100 |
| pH | 9.8 |

In general, skin is mostly composed of keratin cells, and as such an experiment was designed that uses keratin powder as a representative of a skin protein. This simple analysis basically evaluates how the keratin cells behave when in contact with face cleansers in order to evaluate skin mildness. If the keratin cells swell and expand overtime, this equates to a negative impact a face cleanser has on keratin. However, if the cells remain virtually unchanged, then the face cleanser has nearly no impact on the skin and is considered "mild to the skin". Keratin swelling often facilitates release of lipids and a natural moisturizing factor (NMF=blends of lipids, cermainde, collagen etc.) from the skin, leading to skin damage/dehydration.

Toward this end, four experiments were performed using keratin cells that were in contact with three aqueous diluted solutions of face cleansers and a water-only control sample.

Protocol

Keratin powder was mixed with a 10% solution of a foaming cleanser, and the mix was incubated at 40° C. for 24 hours. The powder was then observed under a microscope to assess the morphological aspect of the cells after being in contact with the aqueous solutions of cleansers and were also compared to a powder in water-only sample.

Results and Conclusion

Microscopic images are obtained from of keratin powder in water (reference example—sample A), composition 1B of example 1 (sample B), and comparative example 5.1 as defined above (sample C).

Sample A clearly demonstrates that the keratin cells remain unaffected without swelling. Regarding sample B according to the invention, the keratin powder remained in its original shape after 24 h, indicating that the present claimed composition can be considered "mild to the skin". In contrast, the keratin cells swelled after being exposed to the comparative composition, i.e. a harsher soap only system (sample C).

EXAMPLE 6: HYDRATION AND TRANSEPIDERMAL WATER LOSS (TEWL) MEASUREMENTS AFTER CLEANSING

Tests were performed to evaluate and compare composition 1B of example 1 with the comparative composition 5.1 as detailed in example 5.

Hydration and TEWL were measured on the forearm after rinsing off the samples in order to evaluate the impact of cleansers on skin. Two samples were evaluated: composition 1B of example 1 compared to comparative composition as defined above.

Protocol

1. Models (N=16) wait in a standard condition for certain period of time for T0 data acquisition.

2. The technician randomly applies a fixed amount of products per area of forearm of the models according to the random table; rinses this area with a controlled amount of demineralized water; then wipes with a paper tissue.

3. TEWL of their forearms are measured at a certain period of time.

Reference samples containing water-only were used to obtain baseline measurements.

Results

The following table gathers the data on variation of hydration and TEWL on forearm over time for composition 1B of example 1 and comparatively for comparative composition 5.1 as defined in example 5 above. Two reference samples of water-only were also compared. Hydration measurements were conducted over a period of 15 minutes following the protocol above.

TABLE 2

|  | 0 min (before wash) | 2 min | 5 min | 10 min | 15 min |
|---|---|---|---|---|---|
| TEWL (g/hm2) | | | | | |
| Composition B of example 1 | 4.35 ± 0.59 | 8.43 ± 1.35 | 5.21 ± 0.61 | 4.12 ± 0.625 | 4.34 ± 0.435 |
| Ref of composition B (water only) | 4.33 ± 0.625 | 6.59 ± 1.15 | 4.9 ± 0.565 | 4.48 ± 0.59 | 3.97 ± 0.49 |
| Comparative composition in example 5 | 4.08 ± 0.52 | 11.26 ± 1.77 | 6.38 ± 1.06 | 4.86 ± 0.56 | 3.88 ± 0.65 |
| Ref of comparative composition (water only) | 4.03 ± 0.465 | 6.03 ± 0.87 | 4.34 ± 0.455 | 3.86 ± 0.475 | 3.78 ± 0.645 |
| Hydration (—) | | | | | |
| Composition B of example 1 | 29.04 ± 2.575 | 35.63 ± 2.195 | 32.69 ± 2.345 | 30.63 ± 2.84 | 32.21 ± 5.58 |
| Ref of composition B (water only) | 27.96 ± 2.54 | 33.04 ± 2.095 | 31 ± 2.07 | 29.9 ± 2.255 | 30.63 ± 5.02 |
| Comparative composition in example 5 | 27.13 ± 3.485 | 34.73 ± 2.52 | 31.48 ± 2.94 | 29.73 ± 3.18 | 30.83 ± 6.13 |
| Ref of comparative composition (water only) | 27.67 ± 3.975 | 31.11 ± 2.975 | 28.94 ± 3.07 | 28.5 ± 3.015 | 30.52 ± 6.81 |

Conclusion

It is important to note that the comparative composition must be compared its reference: water-only, while composition 1B of example 1 must be compared to its water-only sample because each Model during the study has a different biological response to water in general.

At the 2 minute mark, the results showed significant increase in hydration for the comparative composition (soap cream sample) compared to its water-only sample. This immediate hydration can be correlated possibly to the swelling of the skin, i.e. negative impact. This swelling is somewhat related to the in vitro keratin test showed above in the images (Sample D). This swelling ultimately can lead to a significant increase in TEWL, which can be correlated to the body's response mechanism to some modification at the skin surface. This in fact is what was observed in the table 3 at time=2 minutes, in which the TEWL for the comparative composition is higher than its reference. This suggests that the comparative composition is more harsh to the skin than water-only.

For the inventive composition 1B of example 1, one can see a similar trend for the hydration experiments; however, the TEWL value difference between composition 1B of example 1 and its reference is smaller than that of comparative composition compared to its reference at times equal to 2, 5, and 10 minutes. It is concluded that composition 1B of example 1, therefore, impacts the skin's biology less than comparative composition, and that composition 1B of example 1 could be considered "milder to the skin" than comparative composition.

EXAMPLE 7: TEST ON THE PARTICLE DEPOSITION OF A ANTI-SHINE COMPOSITION ACCORDING TO THE INVENTION

Protocol

Visual characterization by microscopy was used to observe particle deposition on the skin. More specifically, talc deposition on forearm was observed under high magnification from the scanning electron microscope (SEM) using a tape stripping method. Basically, the forearm was first cleaned with ethanol to remove any impurities from the skin, and then washed using two formulas containing 5% talc with and without Aculyn 38 (composition 2A of Example 2). The foam that was prepared from a cleanser described in the invention was used on the clean surface of the forearm. After using a standardized rinsing protocol, the forearm was dried for 5 min. In order to microscopically observe the particle deposition on the skin, an adhesive tape was attached on the treated area of the forearm, and then removed. The tape strip was then observed under SEM.

Evaluation Results

SEM images on forearm—tape stripping was performed on two formulas. Both formulas contain talc particles; however, one of the images (1) was taken after using the formula containing Aculyn 38, while another image (2) had no thickener (comparative composition 1 of example 2). No image is appended.

Image (1) shows that talc is deposited because the image comprises white 'square' particles above skin cells.

Image (2) does not comprise such white 'square', showing that no talc particles remain on skin cells in image.

Conclusion

The SEM images indicate that the soap-rich formula without thickener did not deposit particles whereas the formula with Aculyn 38 (composition 2A of example 2) allowed particle deposition, indicating that microgel type of thickening polymer is also necessary for talc deposition.

EXAMPLE 8: SKIN FINISH TEST: PERCEIVED SKIN FEEL AFTERSKIN WASHING WITH A MOISTURIZING COMPOSITION ACCORDING TO THE INVENTION

Protocol

Internal panelists were asked to wash their face once with the formulas containing the different amounts of oil, and then were asked to evaluate the skin tightness, dryness, and hydration using a scale of 1-5 after a certain period of time.

The tested formula=composition 3B of example 3 (10% Shea butter) and composition 3C of example 3 (20% Shea butter), and comparative example 3.1 of example 3 (0% Shea butter)

Evaluation Results

In order to test the perceived skin finish, skin attributes (tightness, dryness and moisturized) were monitored by panelists after product usage on the face. The three tables below describe the skin attributes versus time (up to 10 minutes) for the three formulas. The same formula were tested as described in the above section except were applied to the face as opposed to the forearm.

TABLE 3

Variation of skin tightness, dryness and hydration as a function of time

|  | 1 min | 2 min | 5 min | 10 min |
|---|---|---|---|---|
| skin tightness | | | | |
| comparative example 1 of example 3 | 2.8 ± 0.5 | 3.2 ± 0.55 | 3.7 ± 0.65 | 4.1 ± 0.5 |
| composition B of example 3 | 2.1 ± 0.65 | 2.3 ± 0.7 | 3.1 ± 0.7 | 3.3 ± 0.65 |

TABLE 3-continued

Variation of skin tightness, dryness and hydration as a function of time

|  | 1 min | 2 min | 5 min | 10 min |
|---|---|---|---|---|
| composition C of example 3 Dryness | 1.8 ± 0.3 | 2.2 ± 0.45 | 2.5 ± 0.5 | 2.9 ± 0.6 |
| comparative example 1 of example 3 | 2.9 ± 0.45 | 3.4 ± 0.4 | 3.7 ± 0.45 | 4.1 ± 0.45 |
| composition B of example 3 | 2.2 ± 0.6 | 2.8 ± 0.7 | 3.5 ± 0.6 | 3.7 ± 0.65 |
| composition C of example 3 | 2 ± 0.55 | 2.5 ± 0.55 | 2.6 ± 0.5 | 2.9 ± 0.6 |

The formula with no oil was used as a reference and compared with the formula containing 10% and 20% oil.

Conclusion

The formulas containing 10 and 20% Shea butter oil demonstrated a perceived increase in moisturization compared to the 0% comparative composition, and a decrease in skin tightness and dryness over a 10 minute trial period. This perceived moisturization is due to oil deposition on skin after rinse off.

The invention claimed is:

1. Composition containing, in a physiologically acceptable medium:
   a surfactant system comprising (i) at least one N—(C6-30)acyl-amino based surfactant, and (ii) at least one amphoteric surfactant chosen from betaines or (C8-C20)alkyl betaines, (C8-C20)alkylamido(C1-C6)alkylbetaines, and mixtures thereof;
   at least one non-associative crosslinked copolymers of (meth)acrylic acid, and of (C1-C4)alkyl esters of (meth)acrylic acid; and
   a triglyceride oil,
   wherein said N—(C6-C30)acyl-amino based surfactant being present in the surfactant system in a major weight amount, and the surfactant system being present in the composition in an amount of less than 15% by weight relative to the total weight of the composition.

2. Composition according to claim 1, wherein said composition is a foaming cleanser composition.

3. Composition according to claim 1, wherein said composition is a cosmetic composition.

4. Composition according to claim 1, wherein the N—(C6-C30)acyl-amino based surfactant is chosen among N—(C6-C30)acyl aminoacid based surfactant selected from potassium N-cocoyl glycinate and sodium N-cocoyl glycinate.

5. Composition according to claim 1, wherein the N—(C6-C30)acyl-amino based surfactant is present in the composition in an amount ranging from 0.1 to 6% by weight, with respect to the total weight of the composition.

6. Composition according to claim 1, wherein the N—(C6-C30)acyl-amino based surfactant is present in the composition in an amount ranging from 2 to 4% by weight, with respect to the total weight of the composition.

7. Composition according to claim 1, wherein the amphoteric surfactant chosen from betaines or (C8-C20)alkyl betaines, (C8-C20)alkylamido(C1-C6)alkylbetaines, and mixtures thereof is chosen among coco betaine, lauryl betaine, oxyethylenated (10 EO) lauryl betaine, oxyethylenated (10 EO) stearyl betaine, cocamidopropyl betaine, lauramidopropyl betaine and mixtures thereof.

8. Composition according to claim 1, wherein the amphoteric surfactant chosen from betaines or (C8-C20)alkyl betaines, (C8-C20)alkylamido(C1-C6)alkylbetaines, and mixtures thereof is present in the composition in an amount ranging from 0.1 to 6% by weight, with respect to the total weight of the composition.

9. Composition according to claim 1, wherein the amphoteric surfactant chosen from betaines or (C8-C20)alkyl betaines, (C8-C20)alkylamido(C1-C6)alkylbetaines, and mixtures thereof is present in the composition in an amount ranging from 1 to 4% by weight, with respect to the total weight of the composition.

10. Composition according to claim 1, in which the surfactant system further comprises at least one foaming surfactant chosen from anionic, amphoteric, nonionic and/or cationic foaming surfactants, and mixtures thereof, the said anionic surfactant being chosen from anionic derivatives of proteins of plant origin or of silk proteins, phosphates and (C6-C30)alkyl phosphates, (C6-C24)alkyl ether carboxylates, (C6-C24)alkyl(amido) ether carboxylates, (C6-C30) alkylsulfosuccinates, (C6-C30) alkyl ether sulfosuccinates, (C6-C30) alkylamidesulfosuccinates, (C6-C30) acyl or alkyl acids, (C6-C30)alkyl sulfates, (C6-C30)alkyl ether sulfates, (C6-C30)alkylamido ether sulfates, (C6-C30)alkylaryl polyether sulfates, monoglyceride sulfates, (C6-C30)alkyl sulfonates, (C6-C30)alkylamidosulfonates, (C6-C30)alkylarylsulfonates, (C6-C30)α-olefinsulfonates, paraffin sulfonates, (C6-C24)acyl isethionates, taurates, (C6-C30)alkyl sulfoacetates, polypeptides, anionic derivatives of (C6-C30) alkyl polyglucoside, and soaps, and mixtures thereof, the said amphoteric or zwitterionic surfactant being chosen from sulfobetaines, (C8-C20)alkylsulfobetaines, (C8-C20)alkylamido(C1-C6)alkylsulfobetaines, (C8-C20)alkylamphoacetates and (C8-C20)alkylamphodiacetates, and the said nonionic surfactant being chosen from alkyl polyglucosides, oxyalkylenated glycerol esters and oxyalkylenated sugar esters, and mixtures thereof, and the said cationic surfactant being chosen from optionally polyoxyalkylenated primary, secondary or tertiary fatty amine salts, quaternary ammonium salts, quaternary ammonium salts of imidazolinium, and amine oxides of cationic nature, and mixtures thereof.

11. Composition according to claim 1, in which the surfactant system further comprises at least one non foaming surfactant chosen from (C8-C20) fatty acids, mono-, di-, or tri-esters of (C6-C30) fatty acids and of (poly)glycerol, lecithins and mixtures thereof.

12. Composition according to claim 1, wherein the non-associative crosslinked copolymers of acrylic acid and/or methacrylic acid, and optionally of (C1-C4)alkyl esters thereof, is selected from a crosslinked copolymer of acrylic acid and/or methacrylic acid and of an ester thereof comprising less than 6 carbon atoms, a crosslinked copolymer comprising at least one methacrylic unit and at least one $C_1$-$C_4$ alkyl acrylate unit, a crosslinked copolymer of vinyl neodecanoate and one or more monomers of acrylic acid, methacrylic acid or one of their (C1-C4)alkyl esters crosslinked with an allyl ether of trimethylolpropane or pentaerythritol, and mixtures thereof.

13. Composition according to claim 1, comprising a salt of $C_8$-$C_{20}$ fatty acid.

14. Composition according to claim 13, wherein the salt of $C_8$-$C_{20}$ fatty acid is selected among a salt of caproic acid, capric acid, caprylic acid, oleic acid, linoleic acid, lauric acid, myristic acid, stearic acid, palmitic acid and mixtures thereof.

15. Composition according to claim 13, wherein the salt of $C_8$-$C_{20}$ fatty acid is present in the composition in an amount ranging from 0.1 to 6% by weight, with respect to the total weight of the composition.

16. Composition according to claim 1, wherein the triglyceride oil is selected from an oil, a butter, and mixtures thereof.

17. Composition according to claim 1, wherein the triglyceride oil is selected from jojoba oil, babassu oil, sunflower oil, olive oil, canola oil, coconut oil, meadowfoam seed oil, Brazil nut oil, marula oil, maize oil, argan oil, soybean oil, marrow oil, grapeseed oil, linseed oil, sesame oil, hazelnut oil, apricot oil, macadamia oil, arara oil, coriander oil, castor oil, avocado oil, shea butter oil, rapeseed oil, copra oil, shea butter, Nilotica shea butter, galam butter, Borneo butter or fat or tengkawang tallow, shorea butter, illipe butter, madhuca butter, *Madhuca longifolia* butter, mowrah butter, katiau butter, phulwara butter, mango butter, murumuru butter, kokum butter, ucuuba butter, tucuma butter, painya butter, coffee butter, apricot butter, macadamia butter, grapeseed butter, avocado butter, olive butter, sweet almond butter, cocoa butter, sunflower butter, and mixtures thereof.

18. Composition according to claim 1, wherein the triglyceride oil is selected from sheabutter, olive oil, canola oil, meadowfoam seed oil and mixtures thereof.

19. Composition according to claim 1, comprising at least a filler chosen among thickening inorganic or organic particles.

20. Composition according to claim 18, wherein the filler is selected from inorganic particles chosen among silica, hydrated silica, microcrystalline cellulose, polyolefin particle, perlite, clays, ceramic beads, calcium carbonate, titanium oxides, talc or magnesium silicate, kaolin or aluminium silicate, perlite, kaolin and mixtures thereof or from organic fillers, such as starches, maize starch, Nylon microspheres, microspheres based on vinylidene chloride/acrylonitrile/methacrylonitrile copolymer including isobutane, expanded microspheres, micronized or nonmicronized plant, polytetrafluoroethylene powders; acrylic copolymer powders; polyethylene powders; polyamide powders; powders and mixtures thereof.

21. Foaming cleanser cosmetic composition according to claim 1, comprising at least one polyol comprising from 2 to 20 carbon atoms.

22. Foaming cleanser cosmetic composition according to claim 21, wherein the polyol comprising from 2 to 20 carbon atoms is glycerine.

23. Cosmetic method consisting in applying to keratin materials a composition as defined in claim 1 for removing makeup and/or cleansing the skin, the hair and/or mucous membranes, or for skincare.

24. Process for cleansing keratin materials, which consists in applying to the said keratin materials a composition according to claim 1, in working the said composition into a foam and then in rinsing off the said composition.

* * * * *